United States Patent
Stefanchik et al.

(10) Patent No.: US 7,815,565 B2
(45) Date of Patent: Oct. 19, 2010

(54) ENDCAP FOR USE WITH AN ENDOSCOPE

(75) Inventors: David Stefanchik, Morrow, OH (US); Duane Linenkugel, Cincinnati, OH (US); Gregory J. Bakos, Mason, OH (US); Omar J. Vakharia, Mason, OH (US); James A. Craft, Lexington, KY (US); Kurt R. Bally, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/440,956

(22) Filed: May 16, 2003

(65) Prior Publication Data

US 2004/0230097 A1    Nov. 18, 2004

(51) Int. Cl.
*A61B 1/04* (2006.01)

(52) U.S. Cl. .................. 600/121; 600/104; 600/106; 600/107; 600/114; 600/122; 600/123; 600/127; 600/129; 600/153

(58) Field of Classification Search ................. 600/104, 600/121, 123, 127, 129, 153
See application file for complete search history.

(56) References Cited

U.S. PATENT DOCUMENTS

| | | | | |
|---|---|---|---|---|
| 3,915,157 | A | * | 10/1975 | Mitsui .................. 600/107 |
| 4,436,087 | A | * | 3/1984 | Ouchi .................. 600/106 |
| 4,646,722 | A | | 3/1987 | Silverstein et al. |
| 4,686,965 | A | | 8/1987 | Bonnet et al. |
| 4,721,097 | A | | 1/1988 | Amelio |
| 4,773,394 | A | | 9/1988 | Reichstein et al. |
| 4,947,827 | A | | 8/1990 | Opie et al. |
| 5,025,778 | A | * | 6/1991 | Silverstein et al. .......... 600/104 |
| 5,217,001 | A | | 6/1993 | Nakao et al. |
| 5,390,663 | A | * | 2/1995 | Schaefer .................. 600/200 |
| 5,489,256 | A | * | 2/1996 | Adair .................. 600/133 |
| 5,503,616 | A | * | 4/1996 | Jones .................. 600/153 |
| 5,505,686 | A | | 4/1996 | Willis et al. |
| 5,630,782 | A | * | 5/1997 | Adair .................. 600/133 |
| 5,643,175 | A | | 7/1997 | Adair |
| 5,645,519 | A | | 7/1997 | Lee et al. |
| 5,690,620 | A | | 11/1997 | Knott |
| 5,749,889 | A | | 5/1998 | Bacich et al. |
| 5,820,546 | A | * | 10/1998 | Ouchi .................. 600/123 |
| 5,882,293 | A | | 3/1999 | Ouchi |

(Continued)

FOREIGN PATENT DOCUMENTS

EP        1284120 A1    2/2003

(Continued)

OTHER PUBLICATIONS

EPO Search Report dated Aug. 18, 2004 for corresponding patent application, European Patent Application No. EP 04 25 2842.

*Primary Examiner*—Matthew J Kasztejna

(57) ABSTRACT

A guide system for use with an endoscope, and a method of use is disclosed. The guide system can include a track, in the form of a rail, and a mating member for engaging the rail. The guide system can also include an accessory, such as an accessory guide tube through which a medical instrument can be carried external of the endoscope. An end cap can be provided to support the track relative to the distal end of the endoscope.

5 Claims, 18 Drawing Sheets

U.S. PATENT DOCUMENTS

| | | | |
|---|---|---|---|
| 5,944,654 A | 8/1999 | Crawford | |
| 6,059,719 A * | 5/2000 | Yamamoto et al. | 600/127 |
| 6,179,776 B1 * | 1/2001 | Adams et al. | 600/121 |
| 6,238,389 B1 | 5/2001 | Paddock | |
| 6,241,702 B1 | 6/2001 | Lundquist | |
| 6,309,346 B1 | 10/2001 | Farhadi | |
| 6,352,503 B1 * | 3/2002 | Matsui et al. | 600/104 |
| 6,355,034 B2 | 3/2002 | Cosmescu | |
| 6,359,379 B1 | 3/2002 | Lee et al. | |
| 6,527,753 B2 * | 3/2003 | Sekine et al. | 604/264 |
| 6,569,085 B2 * | 5/2003 | Kortenbach et al. | 600/104 |
| 6,689,130 B2 * | 2/2004 | Arai et al. | 606/46 |
| 6,699,180 B2 * | 3/2004 | Kobayashi | 600/127 |
| 6,740,030 B2 * | 5/2004 | Martone et al. | 600/123 |
| 7,081,097 B2 * | 7/2006 | Martone et al. | 600/562 |
| 2002/0107530 A1 * | 8/2002 | Sauer et al. | 606/139 |
| 2002/0183591 A1 * | 12/2002 | Matsuura et al. | 600/127 |
| 2003/0036679 A1 * | 2/2003 | Kortenbach et al. | 600/104 |
| 2003/0130564 A1 * | 7/2003 | Martone et al. | 600/121 |
| 2003/0171651 A1 * | 9/2003 | Page et al. | 600/127 |
| 2003/0176880 A1 * | 9/2003 | Long et al. | 606/167 |
| 2003/0191365 A1 * | 10/2003 | Kobayashi | 600/127 |
| 2004/0230095 A1 | 11/2004 | Stefanchik et al. | |
| 2004/0230096 A1 | 11/2004 | Stefanchik et al. | |

FOREIGN PATENT DOCUMENTS

| | | |
|---|---|---|
| WO | WO 91/14391 A2 | 10/1991 |
| WO | WO 97/29680 A2 | 8/1997 |
| WO | WO 00/48506 A1 | 2/2000 |
| WO | WO 01/49165 A1 | 1/2001 |

* cited by examiner

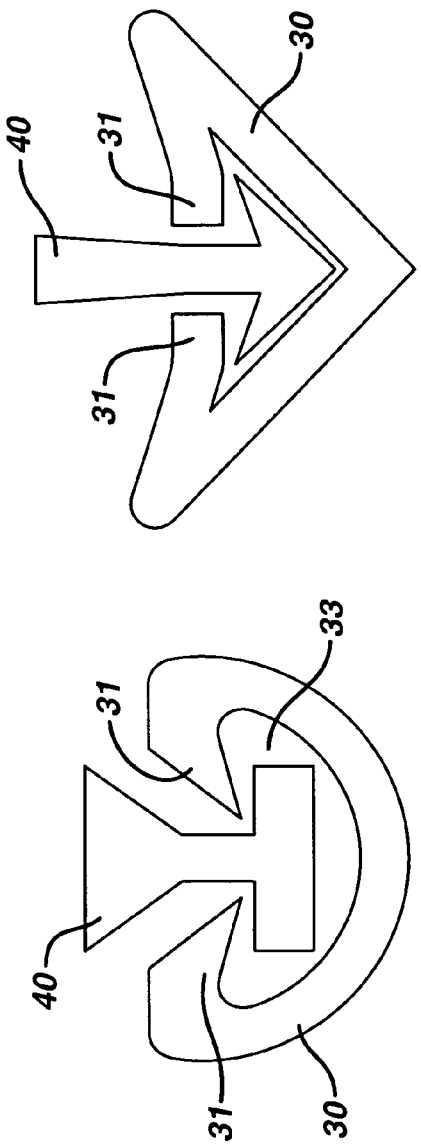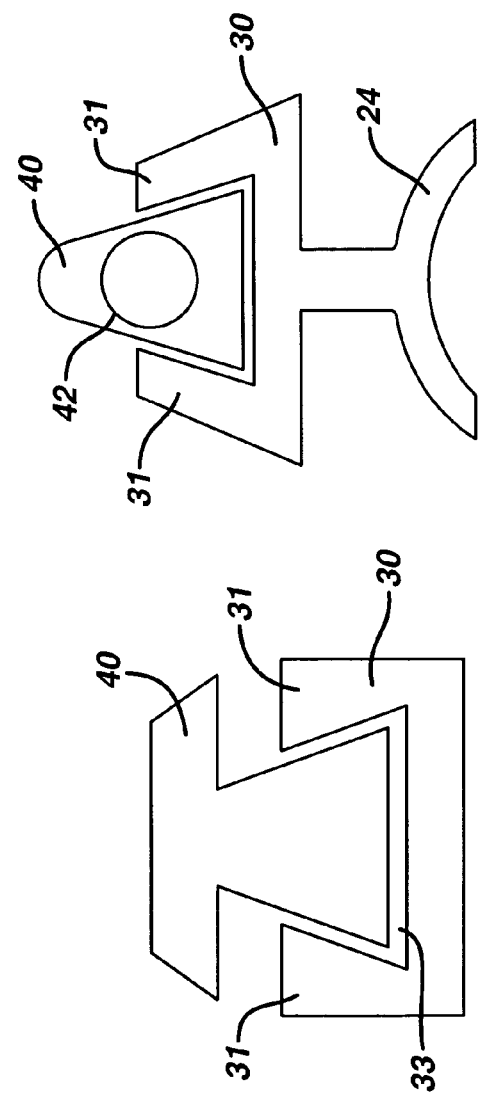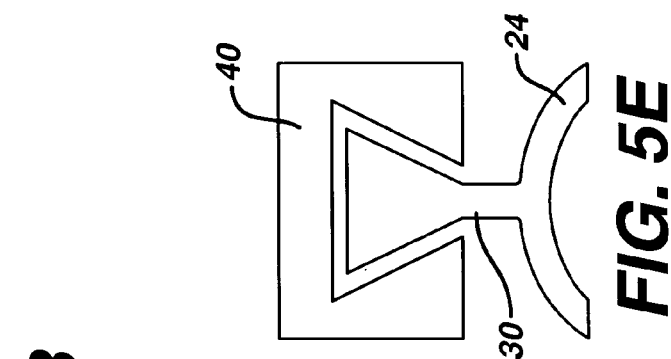

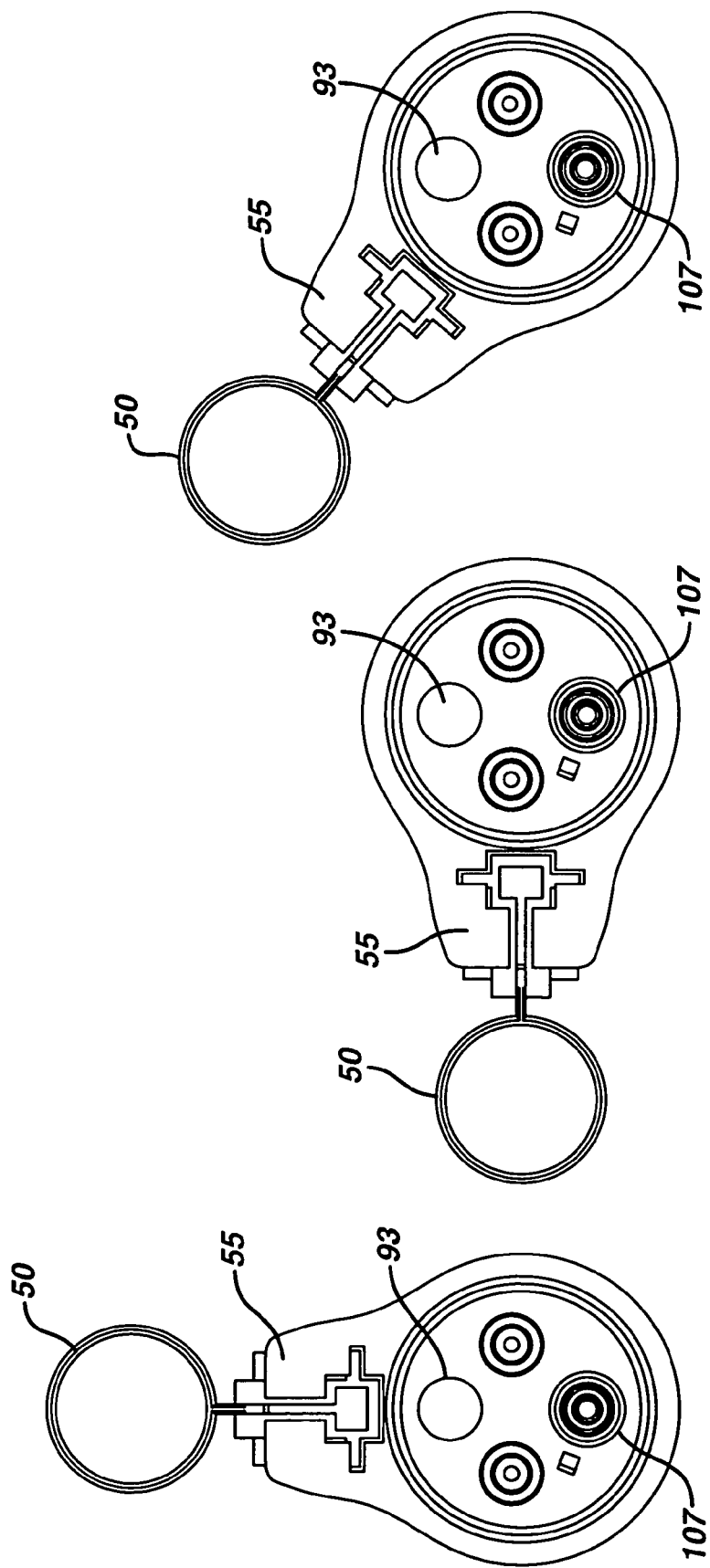

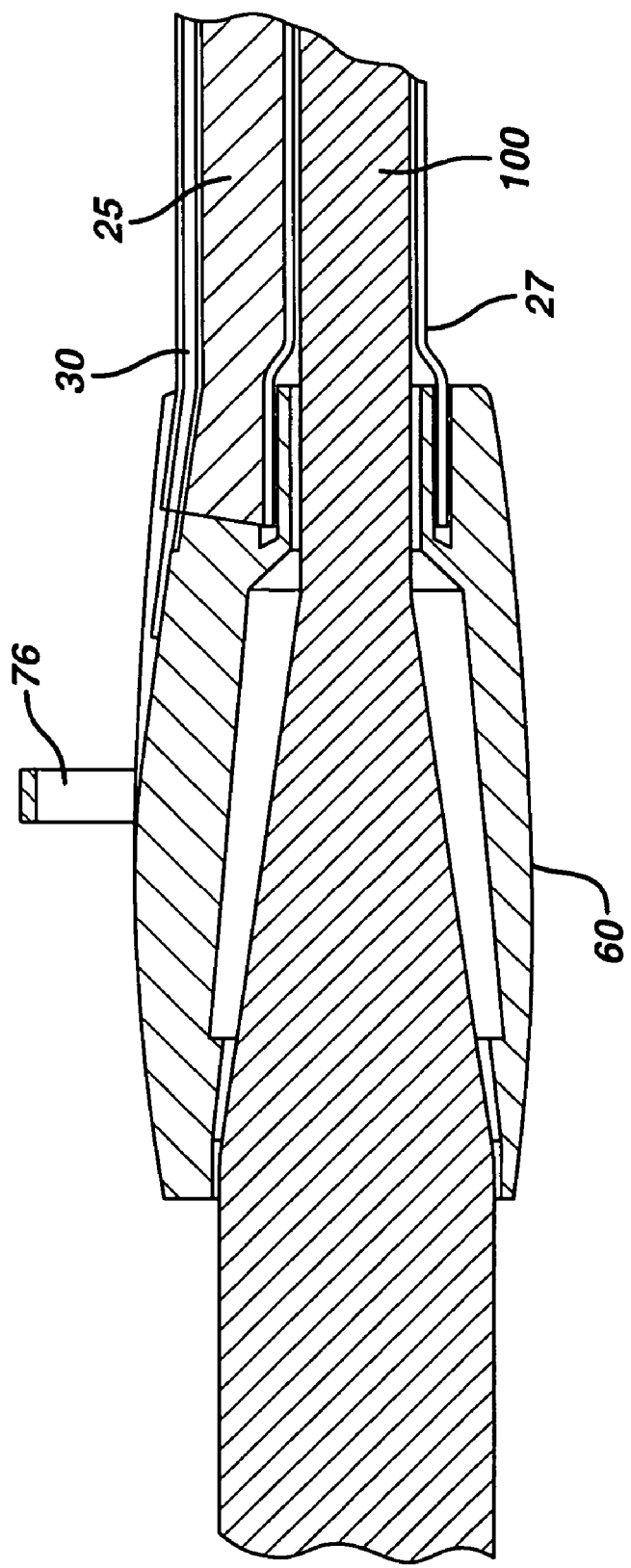

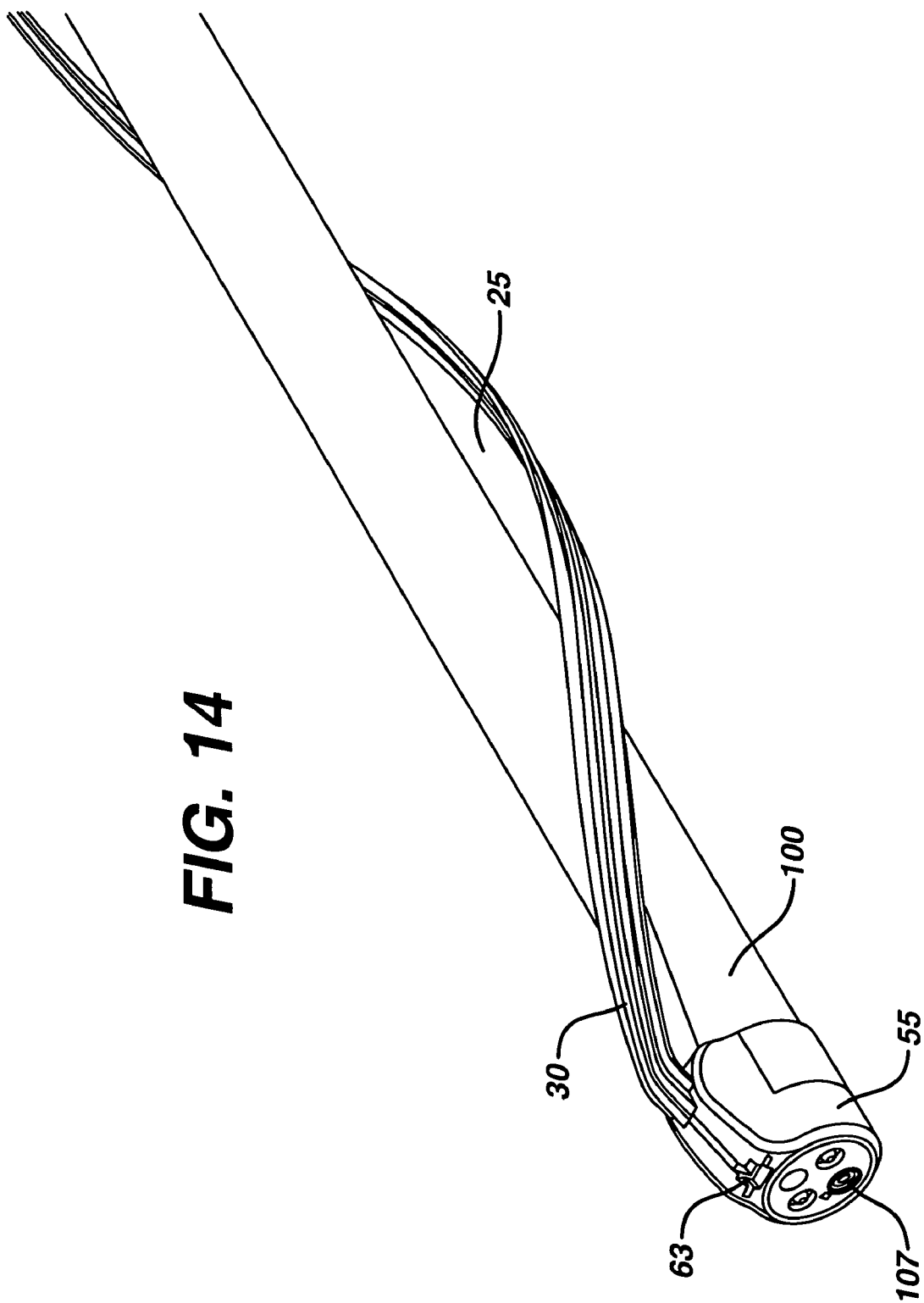

ENDCAP FOR USE WITH AN ENDOSCOPE

CROSS REFERENCE TO RELATED PATENT APPLICATIONS

This applications cross references the following patent applications filed on the same date: Ser. No. 10/440,660, "Method of Guiding Medical Devices", and Ser. No. 10/440,957, "Medical Apparatus for use with an Endoscope".

FIELD OF THE INVENTION

The present invention relates to medical devices, and more specifically to a medical device for use in placement of one or more medical instruments or accessories within a patient's body.

BACKGROUND

Minimally invasive procedures are desirable because such procedures can reduce pain and provide relatively quick recovery times as compared with conventional open medical procedures. Many minimally invasive procedures are performed with an endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall.

Still less invasive treatments include those that are performed through insertion of an endoscope through a natural body orifice to a treatment site. Examples of this approach include, but are not limited to, cystoscopy, hysteroscopy, esophagogastroduodenoscopy, and colonoscopy. Many of these procedures employ the use of a flexible endoscope during the procedure. Flexible endoscopes often have a flexible, steerable section near the distal end that can be controlled by the user by utilizing controls at the proximal end.

Some flexible endoscopes are relatively small (1 mm to 3 mm in diameter), and may have no integral accessory channel (also called biopsy channels or working channels). Other flexible endoscopes, including gastroscopes and colonoscopes, have integral working channels having a diameter of about 2.0 to 3.5 mm for the purpose of introducing and removing medical devices and other accessory devices to perform diagnosis or therapy within the patient. As a result, the accessory devices used by a physician can be limited in size by the diameter of the accessory channel of the scope used. Additionally, the physician may be limited to a single accessory device when using the standard endoscope having one working channel.

Certain specialized endoscopes are available, such as large working channel endoscopes having a working channel of 5 mm in diameter, which can be used to pass relatively large accessories, or to provide capability to suction large blood clots. Other specialized endoscopes include those having two working channels. One disadvantages of such large diameter/multiple working channel endoscopes can be that such devices can be relatively expensive. Further, such large diameter/multiple working channel endoscopes can have an outer diameter that makes the endoscope relatively stiff, or otherwise difficult to intubate.

Various references describe methods or systems that disclose external configurations related to an endoscope, such as for example: U.S. Pat. No. 5,025,778, Silverstein; U.S. Pat. No. 4,947,827, Opie; US 2002/107530 published Aug. 8, 2002 in the name of Sauer; U.S. Pat. No. 6,352,503, Matsui. One disadvantage of known systems is the potential for the distal end of a device used externally of an endoscope to move in a relatively uncontrolled manner, causing the accessory to lack precision or the ability to be maintained within a desired field of view of the imaging capability of the endoscope.

WO 00/48506 published Aug. 24, 2000 in the name of Herrmann discloses a deformable endoscope with at least one supplementary device. The unit comprising the endoscope and the supplementary device is said to have a non-round cross-section. Such a non-circular endoscope may be disadvantageous from the point of view of cost, complexity, or ease in cleaning/sterilization. For instance, a standard endoscope with a smooth, substantially-circular cross section can be relatively easy to sanitize and clean.

WO 00/48506 published Aug. 24, 2000 in the name of Kortenbach, discloses methods and devices for delivering a medical instrument over the exterior of an endoscope to allow the use of instruments too large to fit through the lumena of the endoscope. Kortenbach discloses a collar for use with an endoscope, resilient straps, a flexible sheath having a reclosable seam, flexible polymer extrusions, and a floppy tangential sheath defining a lumen having an irregular (collapsible) cross section. Kortenbach also discloses a track with an inverted T configuration.

SUMMARY OF THE INVENTION

Applicants' have recognized the need for a medical apparatus, such as a disposable medical apparatus, which can be used in connection with an endoscope to place and/or guide accessory medical instruments within the body of a patient, without requiring expensive modifications to the endoscope. Applicants' have also recognized the need for a medical apparatus which can be used in connection with an endoscope to place accessory medical instrument within the body of a patient, without substantially altering the flexibility of the endoscope.

In one embodiment, the present invention provides an end cap adapted to fit on the distal end of an endoscope, wherein the end cap comprises a through bore for receiving the distal end of the endoscope, and wherein the end cap has an outer surface adapted to guide a medical instrument. The end cap outer surface can be adapted to guide a medical instrument relative to an axis of the endoscope.

In one embodiment, the endcap outer surface comprises an inclined surface feature, such as a slot. The surface feature can be useful in guiding a medical instrument relative to an axis of the endoscope. A flexible track can be provided, the flexible track extending proximally from the endcap. The track can have a length of at least 50 cm, more particularly at least about 100 cm.

The endcap can be used in association with a guide system comprising a flexible track. The flexible track can fit into or be otherwise attached to the surface feature on the outside surface of the endcap. In one embodiment, the flexible track can extend intermediate a proximal handle and the endcap. The proximal handle can be used to support the track relative to the proximal portion of the endoscope outside the patient, while the endcap can be used to support the track relative to the distal end of the endoscope inside the patient.

BRIEF DESCRIPTION OF THE DRAWINGS

FIG. 5A-E show cross section views of various embodiments of a rail 30 and a mating member 40.

FIG. 11A-C are front views of end cap 55 placed at different orientations on endoscope 100 in order to change the relative position of accessory 50 with respect to integral channel 93 and lens 107 (and location of convergence point 115).

FIG. 13 shows a cross section view of a proximal end of handle 60 attached to endoscope 100.

FIG. 14 is an isometric view of a distal end of endoscope 100 with rail 30 wrapped around endoscope 100 in a helical arrangement.

DETAILED DESCRIPTION OF THE INVENTION

The present invention is a guide system to facilitate introduction of medical accessories into the body of a patient. By way of example, the present invention is illustrated and described for application in flexible endoscopy in a colon of a human patient. However, the present invention is applicable for use in other medical settings, including but not limited to, rigid endoscopy, laparoscopy, cystoscopy, hysteroscopy, esophagogastroduodenoscopy, sigmoidoscopy, proctoscopy, or enteroscopy in which the body lumens of humans or other mammals are accessed.

Figure 1:
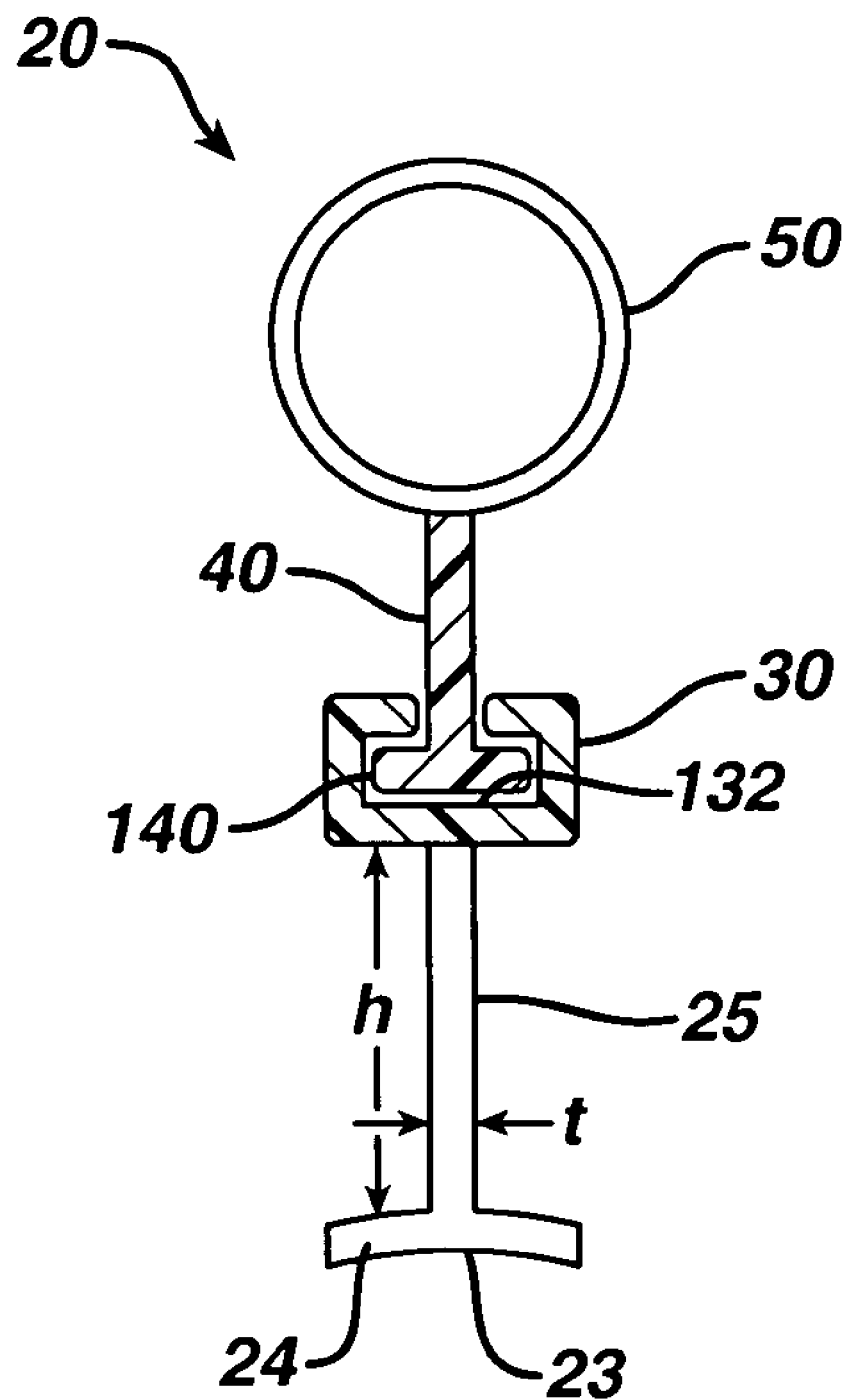
FIG. 1 is a cross-section view of a guide system according to one embodiment of the present invention and showing an accessory 50 attached to a mating member 40, with mating member 40 slidably engaging a rail 30, and with rail 30 attached to a flexible attachment flange 25.

FIG. 1 shows a cross section of one embodiment of a guide system 20 according to one embodiment of the present invention. In FIG. 1, guide system 20 is illustrated as generally comprising a track in the form of guide rail 30, a mating member 40, and an accessory 50. In the embodiment shown in FIG. 1, accessory 50 can be in the form of a flexible tubular guide for receiving and guiding a medical instrument alongside an endoscope. Guide system 20 can be used to facilitate introduction of accessory 50 into the body of a patient by providing a means to slide accessory 50 along the length of another medical instrument, such as an endoscope, in a controlled manner. Rail 30 may be flexibly supported in spaced relationship from the outer surface of the endoscope by a flexible web in the form of flange 25. Flange 25 can have a thickness t of between about 0.005 inch and about 0.030 inch, and a height h of between about 0.020 inch and 1.0 inch. In one embodiment, height h can be between about 0.080 inch and about 0.200 inch, such as in applications related to the use of colonoscopes in colonoscopy. Flange 25 can be formed of a flexible material, such as a flexible plastic material. One suitable material from which flange 25 can be formed is a thermoplastic elastomer, such as a material designated commercially as Telcar 1025-75 (available from Teknor-Apex, Pawtucket, R.I.). Height h provides standoff of accessory 50 from the outside surface of the endoscope. Height h can be selected to be greater than or equal to about one half the outer diameter of the endoscope with which the guide system 20 is used. Without being limited by theory, such a height h may provide the advantage that upon bending/flexing of the endoscope 100, such a height h of the flange 25 can permit the rail 30 to move into approximate alignment with the neutral axis of bending of the endoscope, so that rail 30 does not significantly increase the bending stiffness of the endoscope 100.

Mating member 40 is operatively coupled to rail 30 through interlocking contours. A first contour 140 of mating member 40 can have a substantially matching shape to a second contour 132 of rail 30, so that mating member 40 slides along rail 30. There is a nominal clearance distance between the mating surfaces of mating member 40 and rail 30, so that no binding or pinching occurs when sliding one relative to the other. A nominal clearance of 0.005" may be provided to allow sliding of mating member 40 along rail 30 like a drawer in a drawer slide.

One or both of rail 30 and mating member 40 can be made from a flexible, low friction ("slippery"), plastic material, such as polyethylene, Teflon, or polypropylene to provide a low coefficient of friction between the members as they slide relative to one another. Because the length (as measured perpendicular to the plane of FIG. 1) of guide system 20 is much longer than the width (measured parallel to a horizontal line in the plane of FIG. 1) of the cross section, various components such as rail 30, mating member 40, attachment flange 25, or accessory 50 may be made with an extrusion process, but such a process is not required. Additionally, rail 30 and flange 25 can be formed as a unitary piece, such as by extrusion. Likewise, mating member 40 and accessory 50 can be formed as a unitary piece, or joined by any suitable attachment method. In FIG. 1, flange 25 can include an attachment base 24. Attachment base 24 can provide releasable attachment of the flange 25 to the outer surface of an endoscope. For instance, attachment base 24 can include an adhesive layer on a bottom surface 23, by which flange 25 can be attached to an endoscope. Flange 25 may also be secured to endoscope with adhesive sprays or tapes, Velcro-like attachment materials, non-adhesive silicone tape, with segments of heat shrink tubing, or other suitable attachment means. Such attachments enable rail 30 to be attached to numerous sizes of standard endoscope, allowing guide system 20 to be compatible with standard equipment already owned by a user.

Figure 2A:
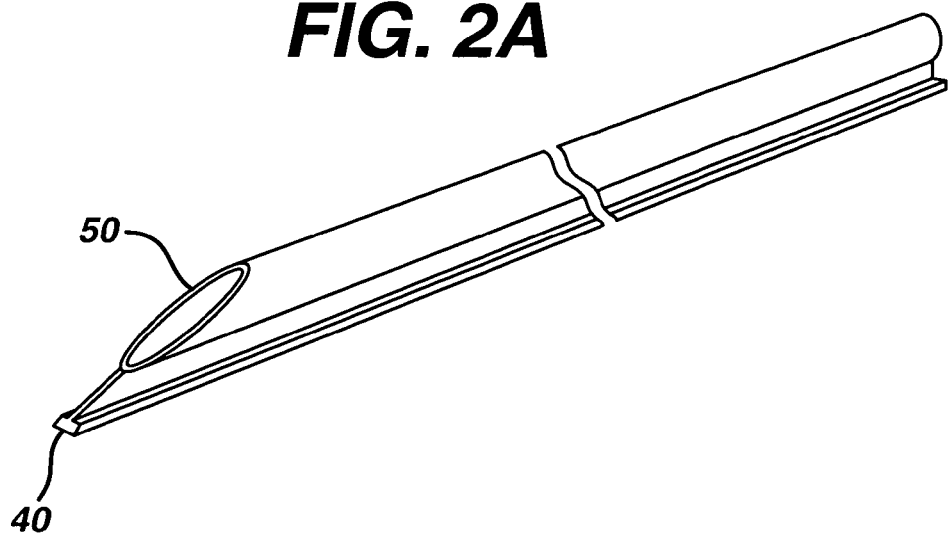
FIG. 2A is an isometric illustration of an accessory guide 50 and a mating member 40 according to an embodiment of the present invention.
Figure 2B:
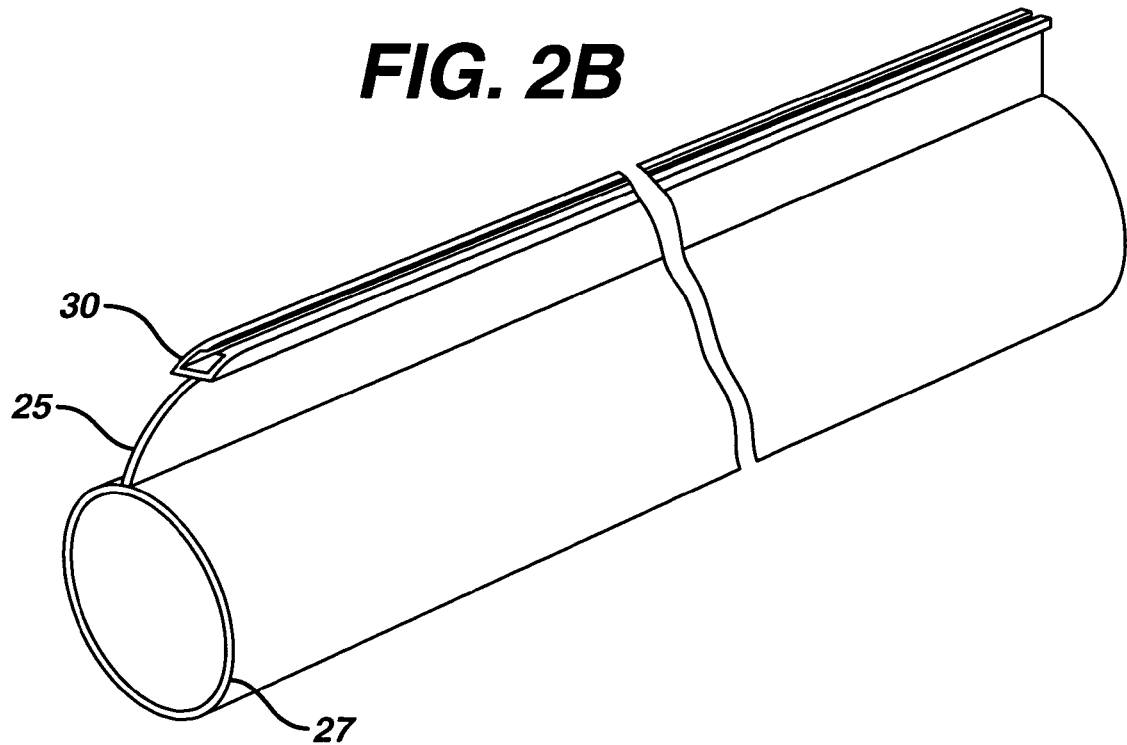
FIG. 2B is an isometric illustration of a rail 30, flange 25, and a thin walled tube or sheath 27, with flange 25 attached to thin walled tube 27 and flange 25 extending generally radially from thin walled tube 27.
Figure 2C:
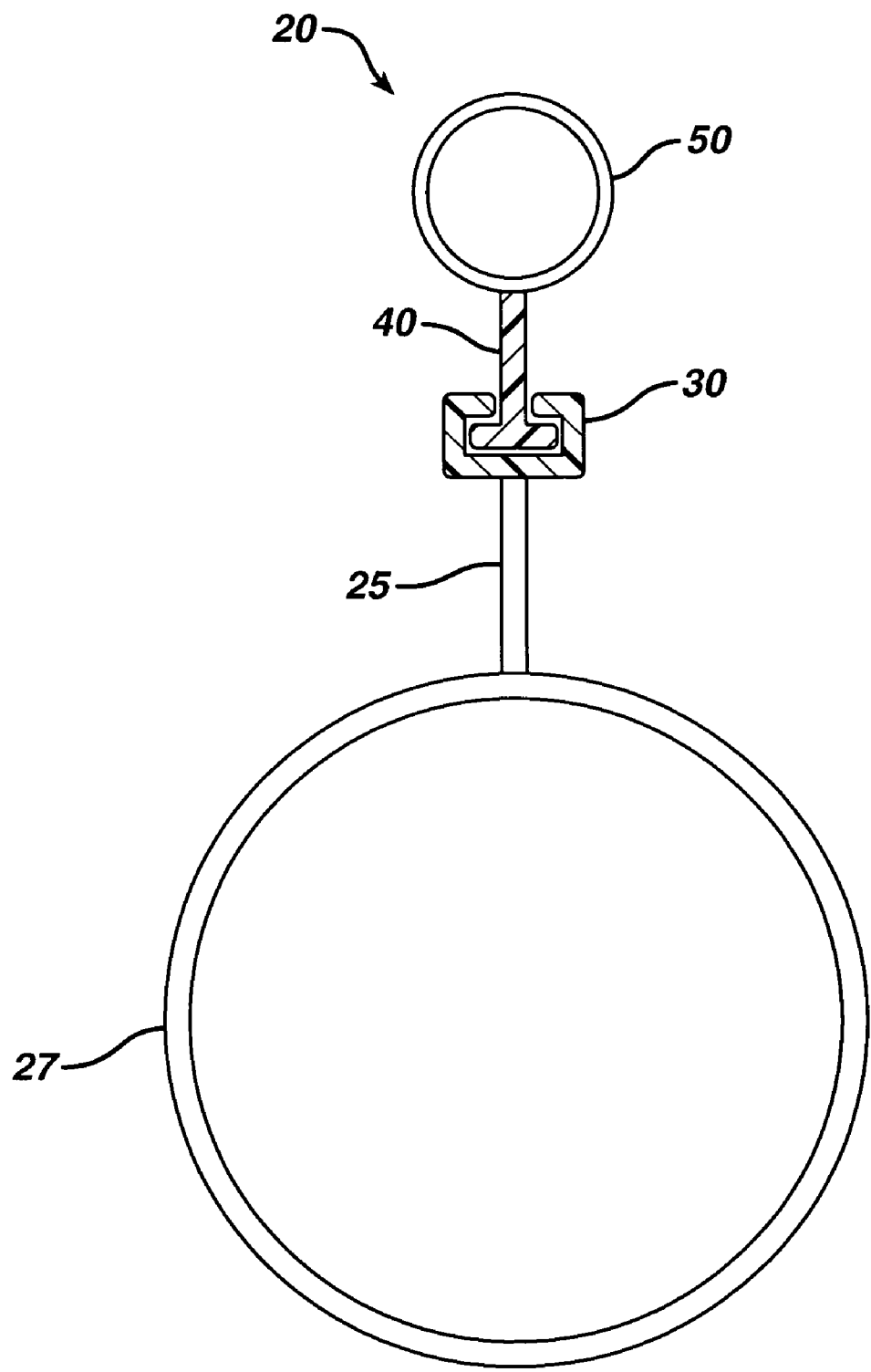
FIG. 2C is a cross-sectional illustration showing accessory guide 50 and flange 25 supported in sliding engagement with rail 30, such that accessory guide 50 is spaced radially from thin wall tube or sheath 27.

FIGS. 2A-2C illustrate another embodiment of a guide system 20 of the present invention. FIG. 2A is an isometric view of the accessory 50 and mating member 40 of a guide system 20. FIG. 2B is an isometric view of the rail 30 and attachment flange 25 associated with a thin wall tube 27. FIG. 2C is cross-sectional view of an assembled guide system 20, including accessory guide 50, mating member 40, rail 30, flange 25, and thin walled tube 27, which can be in the form of a flexible sheath.

In FIG. 2B and FIG. 2C, the attachment flange 25 can be attached to, or be integrally formed with (such as by extrusion) the thin wall tube 27. Thin wall tube 27 is flexible, and can be sized to slide over an endoscope. The guide system 20 of the present invention can have an continuous, uninterrupted length which is substantially the same as the insertion length (length that is meant to go inside the patient) of an endoscope 100. Alternatively, the guide system can have an overall length that is greater than the insertion length of the endoscope 100. In one embodiment, the thin walled tube 27, the flange 25, and the rail 30 can have a continuous, uninterrupted length of at least about 50 centimeters, more particularly at least about 100 cm, and still more particularly at least about 160 cm, such as for work associated with a colonoscope and colonoscopy.

The inner diameter of the thin wall tube 27 can be sized to be slightly greater than the outer diameter of the endoscope 100. Endoscope 100, disposed in the thin wall tube 27, can rotate relative to the tube 27, such as when endoscope 100 is retroflexed or otherwise bent or curved. Such relative rotation of the tube 27 (and so flange 25 and rail 30) with respect to the endoscope can assist in the rail 30 being capable of moving circumferentially relative to endoscope 100 and taking on a position that is approximately aligned with the neutral axis of bending of the endoscope.

The thin walled tube 27 and attachment flange 25 shown in FIGS. 2B and 2C may be made from a flexible plastic, such as thermoplastic elastomer, one example of which is Telcar 1025-75 (Teknor-Apex, Pawtucket, R.I.). The wall thickness of the thin walled tube 27 and attachment flange 25 may be about 0.0020". Although connected to attachment flange 25, rail 30 may be made from a different material, such as polypropylene, which may be used for providing ease of sliding. One suitable polypropylene is Pro-fax 7823 (Basell, Wilmington, Del.). A coextrusion process may be used to form an integral extruded part from at least two different materials, such as with one embodiment of rail 30 and attachment flange 25.

Likewise, similar materials and processes may be used to create accessory 50 attached to mating member 40. For embodiments wherein accessory 50 is in the form of a flexible guide tube, accessory 50 can be made from thermoplastic elastomer, such as Telcar 1025-75 (available from Teknor-Apex of Pawtucket, R.I.). Mating member 40 can be made from a "slippery" low friction material, such as Teflon, polyethylene, or Pro-fax 7823 polypropylene (available from Basell Co. of Wilmington, Del.). Mating member 40 and accessory 50 may be formed through a coextrusion process, or alternatively, may be joined together by any other suitable joining technique.

In use, the rail 30 can be supported on the endoscope prior to insertion of the endoscope into the patient (such as by sliding the thin wall tube or sheath 27 and rail 30 over the endoscope prior to insertion into the patient). Once endoscope 100 is in a position within the body, mating member 40 can be engaged with rail 30, and the mating member 40 and the accessory 50 can then advanced along the length of the endoscope by sliding engagement with rail 30, so that accessory 50 is positioned in or near a field of view 110 (see FIG. 4A) to perform treatment or diagnosis (such as by advancing a medical instrument through accessory 50).

In the embodiments shown in FIGS. 1 and 2A-2C, the guide system 20 couples rail 30 to endoscope during a procedure, but does not substantially stiffen the endoscope, and is removable after the procedure without altering or disassembling endoscope. The embodiments shown in FIG. 1 and FIGS. 2A-C permit the rail and associated accessory guide 50 to be attached to various sizes of standard endoscopes, allowing guide system 20 to be compatible with standard endoscopes already owned by the user, and avoiding the need to purchase additional new specialized capital equipment. Rail 30 can be disposable so that after a single patient use, it can be removed from the Endoscope and discarded with other medical waste. Disposability avoids the requirements for cleaning, which could be difficult and time consuming considering the shape of rail 30 which may incorporate a long narrow groove. Mating member 40 and accessory 50 may also be disposable.

In the embodiments shown, the guide system 20 couples rail 30 and the associated accessory 50 to the endoscope such that flexibility and maneuverability of the endoscope is maintained. By way of example, but without limitation, the guide system of the present invention can be used with a colonoscope without appreciably changing the stiffness of the colonoscope and without appreciably changing the colonoscopes bending axis, due at least in part to the ability of the rail 30 to take on a curved path different from that of the curved endoscope, and the ability of rail 30 to take on a position that is approximately aligned with the neutral axis of bending of the endoscope. Accordingly, the present invention obviates the need to employ a specialized endoscope having a non-circular cross section, or a cross section that is otherwise modified, such as to provide preferential bending or to accommodate the use of accessories along the side of the endoscope.

Referring to FIGS. 2A-2C, guide system 20 can have a mating member 40 and a rail 30 either or both of which is substantially the same length as, or longer than the endoscope with which they are used. Such a configuration allows a user to slide accessory 50 (and any instruments inserted through accessory 50) into a patient's body without relying upon axial stiffness of accessory 50 (or the axial stiffness of the instrument inserted through accessory guide 50). Without being limited by theory, it is believed that mating member 40 and accessory guide 50 can be advanced along rail 30, even though both are flexible, due at least in part to the close clearance between rail 30 and mating member 40 and the continuous, uninterrupted nature of the track provided by rail 30. The embodiments shown permit the insertion of a soft flexible accessory 50, a short accessory 50 that may not inherently possess the rigidity to push it along the side of endoscope 100, or the insertion of a short rigid segment.

Figure 16:
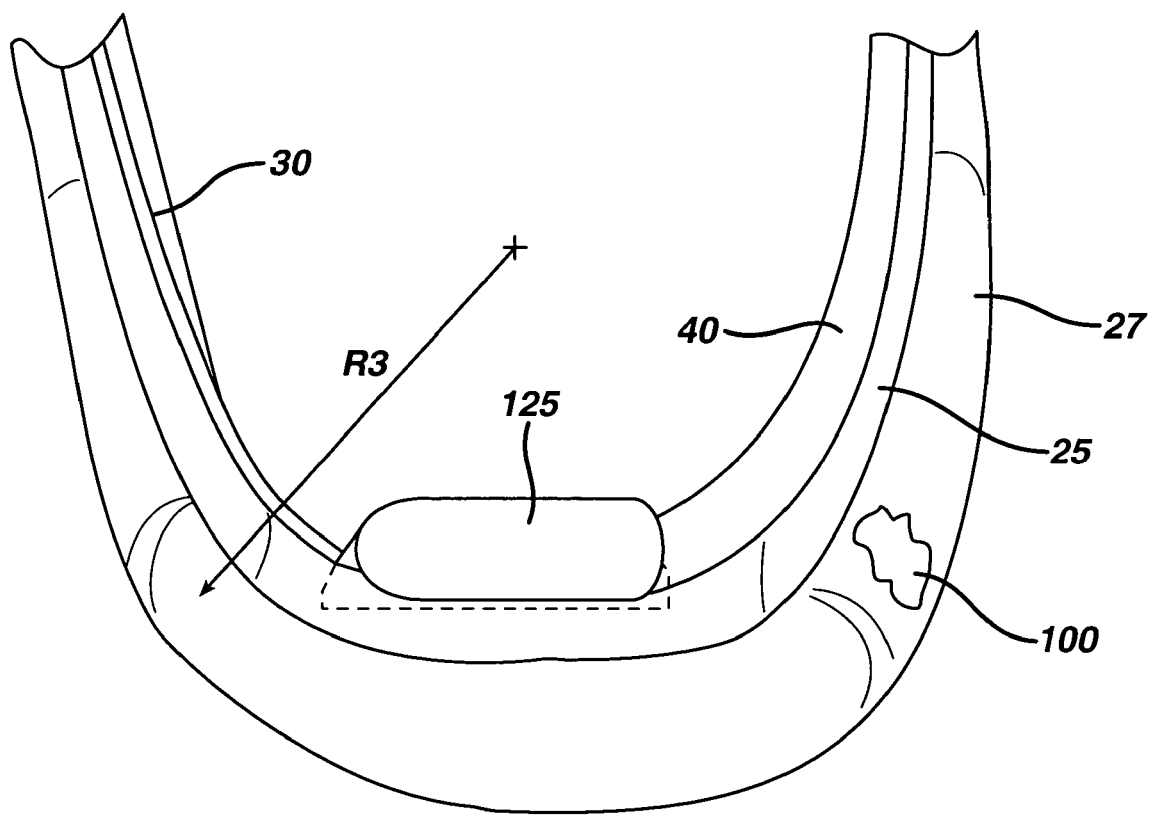
FIG. 16 is a side view showing a short, relatively straight and relatively rigid device 125 supported on and slid along rail 30 along a section of endoscope 100 curved (such as by retroflexing) to have a radius R3.

Guide system 20 also allows for introduction of a short, rigid device 125, as shown in FIG. 16. For example, a commercially available probe such as the BRAVO™ brand pH Monitoring System available from Medtronics of Minneapolis, Minn. has a relatively short (approx 25 mm), relatively rigid segment. The pH monitoring system is a wireless capsule which is attached to the wall of the esophagus for approximately 48 hours, during which data is transmitted to a remote (external to patient) receiver. The guide system of the present invention can be used to deploy the pH monitoring capsule, such as by pushing the capsule through the accessory 50 to the location at which the capsule is to be attached, or by attaching the capsule to the mating member 40 and pushing the capsule by advancing mating member 40 along the length of the endoscope. Alternatively, the rail 30 can have a cross-section that is sized and shaped to permit the device to slide axially along the length of rail 30, while preventing the device from disengaging from the rail.

Flexible flange 25 provides the advantage that a relatively rigid device, (such as for example a generally straight, relatively rigid device) can be pushed by sliding along rail 30, even as the flexible endoscope is retroflexed or otherwise curved. The flexibility of the guide system 20 of the present invention decouples bending of rail 30 from bending of the endoscope, so that a relatively stiff device or accessory, that would otherwise be difficult to slide to the distal end of the endoscope, can be slid along the curved endoscope. FIG. 16 illustrates schematically a relatively rigid device 125 being advanced on rail 30 around a curved segment of endoscope 100.

In another embodiment, accessory 50 can be a device having a length shorter than that of endoscope 100, and not form a working channel. For example, the accessory 50 could be in the form of a hemostatic gauze pad. The gauze pad could be attached to the distal end of the mating member 40, such as by suture, adhesive, staples, or a clip. The gauze could then be used to treat a bleeding site, after which the gauze pad could be pulled from the body by pulling mating member 40 backward (proximally) along the rail 30. The present invention enables one to push a member that is relatively short and/or has low axial stiffness. The guide system 20 of the present invention allows advancement of such devices into a patient at least in part because mating member 40 can provide the axial support and the length needed to move such a device into a patient.

Embodiments of the guide system 20 of the present invention having a mating member 40 with a length that is greater than or substantially equal to the length of rail 30 and the insertion length of the endoscope provide an advantage over endoscopic systems using a engaging member that is not substantially the same length as a track. In such endoscopic systems, a medical instrument to which the engaging member is attached will generally require sufficient axial rigidity to enable pushing of the medical device along the endoscope. Additionally, such endoscopic systems can require a block or "stop" at a distal end of a surface track so that an engaging member is not advanced off the end of the track. In contrast, the embodiments of the guide system 20 of the present invention having a mating member 40 with a length greater than or substantially equal to that of the rail 30 and the insertion length of the endoscope do not require such a block feature, and provide the advantage that accessory 50 can be advanced beyond the end of the endoscope into a field of view of the endoscope, and then retracted.

Figure 3A:
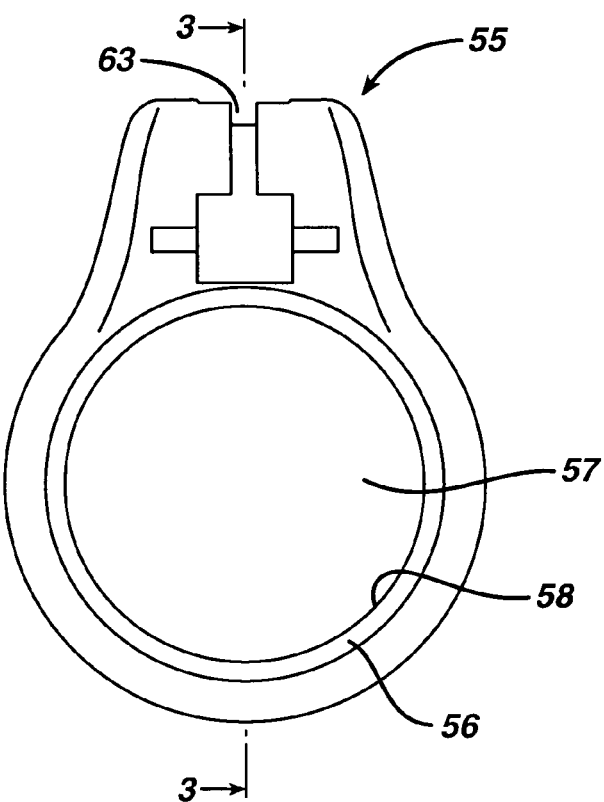
FIG. 3A is a front view of an end cap 55 showing several features including a gripping surface 58 and a guide notch 63.
Figure 3B:
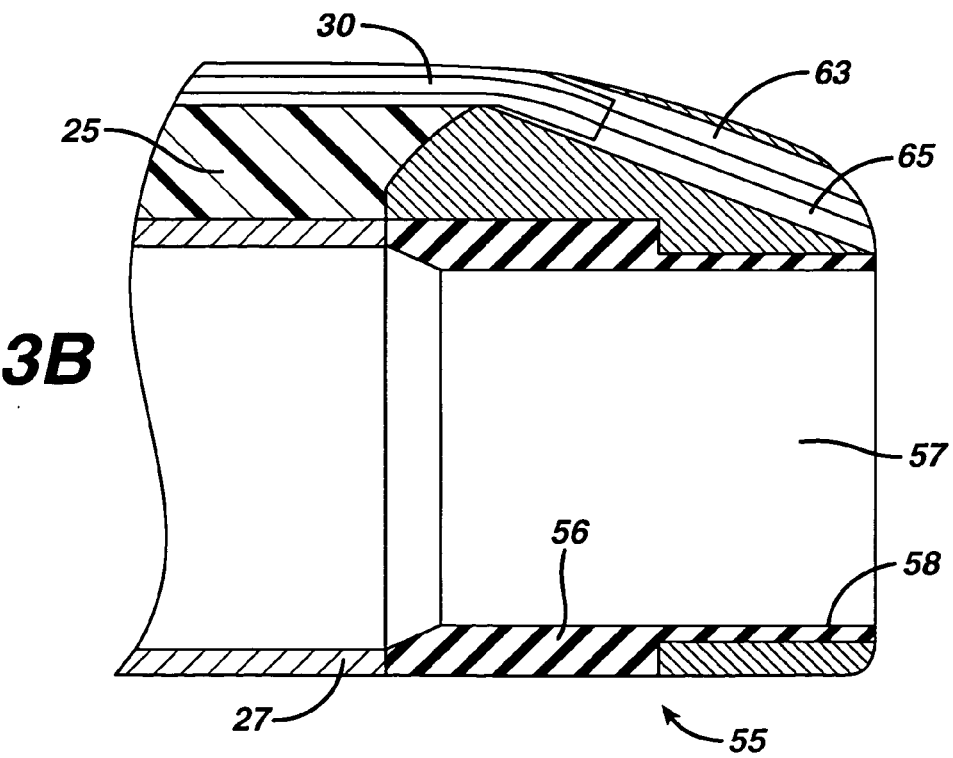
FIG. 3B is a cross section taken at line 3-3 of FIG. 3A showing inclination angle 65.

FIGS. 3A and 3B and FIGS. 4A and 4B illustrate an end cap 55 according to one embodiment of the present invention. FIG. 3A is an end view of the end cap 55, and FIG. 3B is a cross-sectional view taken along section line 3-3 in FIG. 3A. End cap 55 can be a component of a guide system 20 according to one embodiment of the present invention, or alternatively, end cap 55 can be a separate, stand alone accessory. End cap 55 can be configured to be releasably attachable to the distal end of an endoscope 100. By releasably attachable it is meant that end cap 55 can be repeatedly attached to, and removed from, the endscope without damaging either the end cap 55 or endoscope. End caps 55 can be provided in various sizes to fit onto the ends of various diameter endoscopes. End cap 55 can receive the distal end of rail 30, and can help control and guide accessory 50 in a field of view 110 (see FIG. 4A) of endoscope 100.

FIG. 3B shows a cross-section of the junction of the thin wall flexible tube 27, flexible attachment flange 25, and rail 30 to end cap 55. The junction may be accomplished by adhesive joining or any other suitable joining method. A distal portion of the rail 30 can extend and be held by the notch 63 so that the mating member 40 can slide along the outside surface of end cap 55 in a continuous, non-interrupted path.

End Cap 55 can include a relatively rigid external body, and a relatively soft internal insert 56 with a through bore 57. The insert can include a gripping surface 58. Insert 56 and gripping surface 58 can be provided for releasably attaching end cap 55 to endoscope 100, such that end cap 55 is pushed onto the distal end of endoscope 100 without the need for special tools or assembly techniques to attach or remove end cap 55 to the end of the endoscope. The insert and gripping surface 58 may be made from a sticky or tacky material such as silicone or neoprene, or may include adhesive to hold end cap 55 in place on the distal end of the endoscope 100 Alternatively, end cap 55 can be held in place using a snap fit, an interference fit, or any other suitable attachment means which permits end cap 55 to be releasably attached to the distal end of an endoscope. The remainder of the body of end cap 55 including the external body may be made from a biocompatible plastic, such as nylon 6/6, polycarbonate, or polyvinyl chloride (PVC).

End cap 55 can be provided with smooth rounded edges on its external surface, and connects to a distal portion of endoscope 100. The end cap 55 includes a surface feature on its external surface adapted to guide a medical instrument, such as a medical instrument advanced externally along the endoscope (such as in an accessory guide tube 50). The surface feature can be in the form of a slot, such as guide notch 63. Guide notch 63 can be shaped to receive the distal end of rail 30. The distal end of rail 30 can extend into guide notch 63 (FIG. 4A), and the distal end of rail 30 can take on a path determined by the geometry (slope or incline) of guide notch 63, so that the distal end of mating member 40 sliding on rail 30 can follow a path determined by the geometry of guide notch 63. In the embodiment shown, the guide notch 63 is inclined radially inward from the proximal end of the guide notch to the distal end of the guide notch.

In the embodiment shown, guide notch 63 is inclined with respect to the axis of through bore 57 (and so inclined with respect to the longitudinal axis of the endoscope to which end cap 55 is attached). The angle at which guide notch 63 is inclined is indicated by reference numeral 65 to direct accessory 50 into field of view 110. This feature of end cap 55 may be useful to provide convergence of accessory 50 inserted using guide system 20 to an instrument 68 inserted through an integral channel 93 (FIG. 6) of endoscope 100. Depending on the value of angle 65, location of a convergence point 115 (FIG. 8) may change. In one embodiment, angle 65 may be at least about 5 degrees, and more particularly at least about 10 degrees. In one embodiment, the angle 65 can have a value between about 10 degrees and about 30 degrees.

In an alternative embodiment to end cap 55, the flange 25 can be tapered, such as by being tapered radially inwardly (e.g. with the flange height h being reduced at the distal end of the flange 25), so that rail 30 on flange 25 is directed radially inwardly at the distal end of the guide system 20 to guide the accessory 50 both axially and radially inwardly at the distal end of the endoscope 100.

Figure 4A:
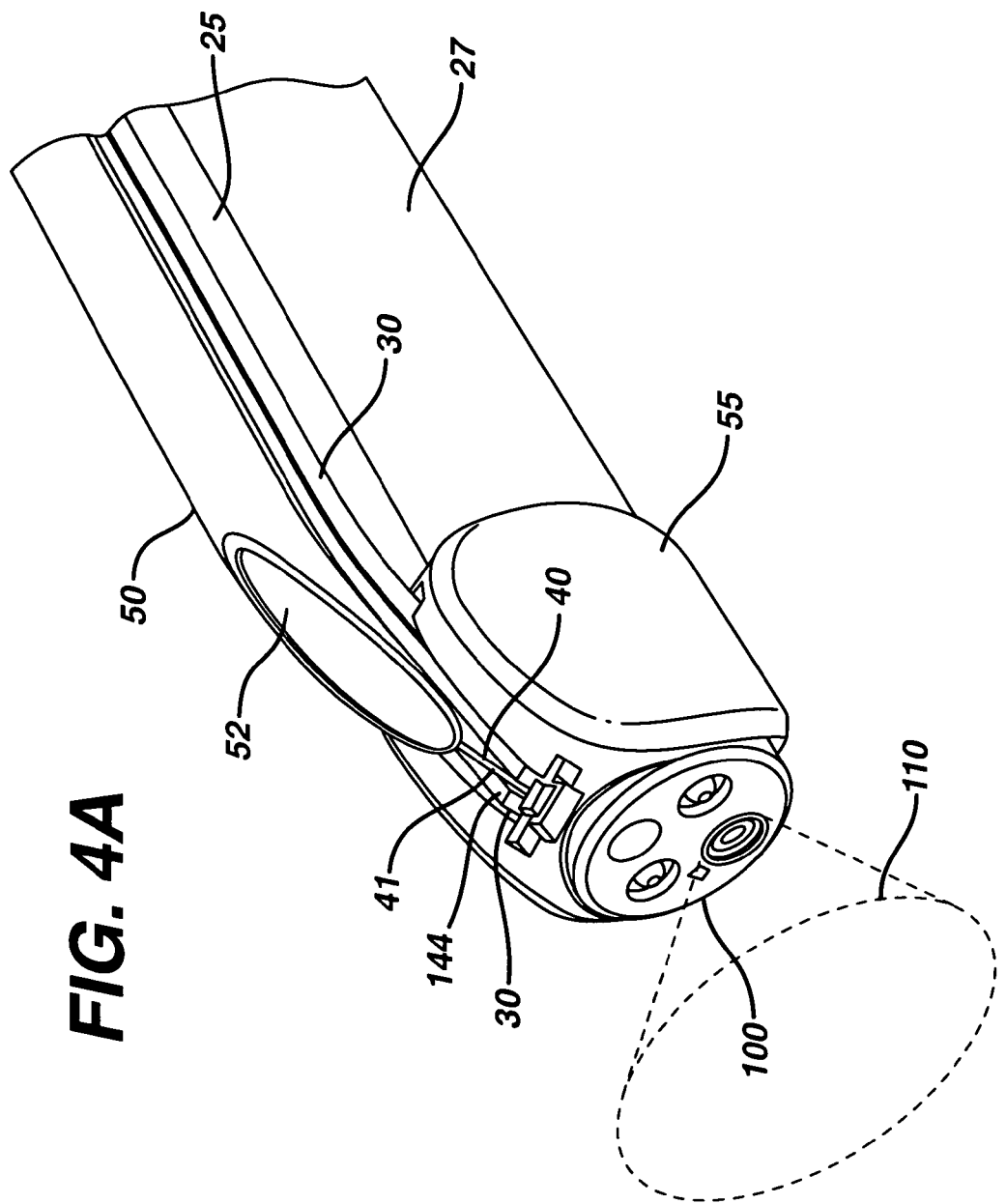
FIG. 4A is an isometric view of the distal end of a guide system 20 in use with an endoscope 100, and showing field of view 110.
Figure 4B:
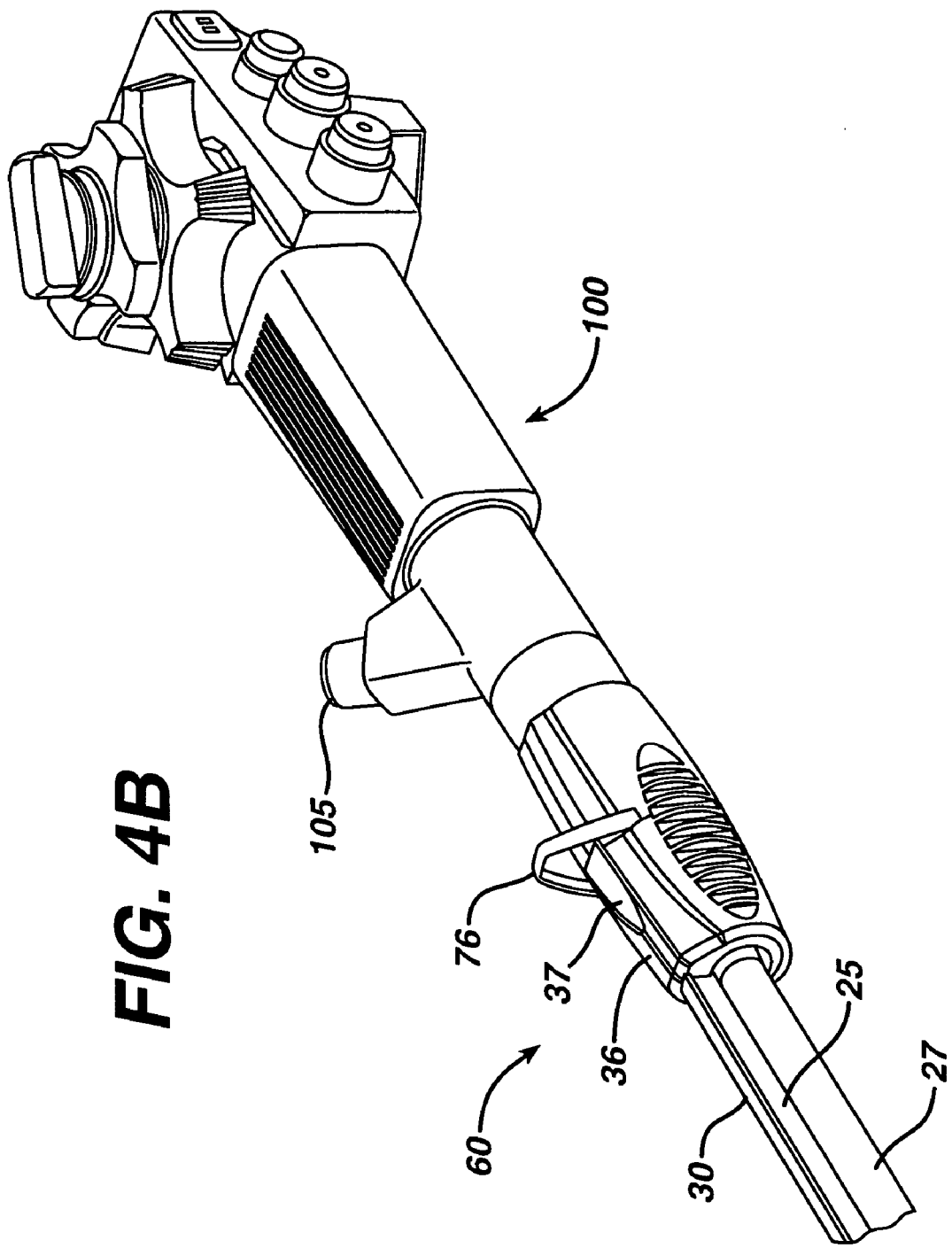
FIG. 4B is an isometric view of the proximal end of the guide system 20 in combination with an endoscope 100.

FIGS. 4A and 4B illustrate distal and proximal ends of guide system 20 attached to endoscope 100. FIG. 4A shows a distal end of guide system 20 with end cap 55, attachment flange 25, thin wall tubular sheath 27, mating member 40, rail 30, and endoscope 100 (extending through bore 57 of end cap 55). In the embodiment shown, accessory 50 is in the form of an external working channel 52. Working channel 52 can receive and guide a variety of medical instruments from a point outside the patient to a position distal of the distal end of the endoscope within the patient.

As shown in FIG. 4A, the leading (distal) end of mating member 40 can have a tapered or an inclined edge 41 shaped to allow atraumatic passage along endoscope 100 inside a patient's body. The interface between rail 30 and mating member 40 can be located to avoid pinching tissue as the mating member 40 slides in rail 30, such as by locating the interface below an outer surface 144 of rail 30. A smooth covering or a tapered nose on the leading edge of accessory 50 can be employed.

FIG. 4B shows one embodiment of a proximal portion of guide system 20, including flexible tubular sheath 27, attachment flange 25, rail 30, and a hollow handle 60. Handle 60 includes a through bore for receiving an endoscope such that the endoscope can pass through handle 60. Handle 60 may be constructed of a soft tacky material, such as neoprene or silicone, and may include a slot 36 formed in handle 60 for receiving the proximal end of rail 30. A funnel feature 37 at the proximal end of slot 36 can be employed to facilitate insertion of mating member 40 into rail 30. Handle 60 may be designed to slide over the distal end of an endoscope 100, and can have an internal conical shaped surface to fit against a proximal portion of endoscope 100, near an introductory port 105 integral to endoscope 100, as shown in FIG. 4B. Introductory port 105 of endoscope 100 receives medical instruments, such as medical instrument 68 shown in FIG. 8. The handle 60 can be permanently fixed to the proximal end of thin wall flexible tube/sheath 27, or alternatively, can be releasably joined to the thin wall tube/sheath 27.

FIG. 13 shows a cross section of the junction of the thin walled tube 27, rail 30, and attachment flange 25 to the handle 60. The connection of the tube 27, rail 30, and flange 25 to handle 60 can be permanent, such by use of adhesive. The subassembly comprising the handle 60, thin walled tube 27, rail 30, flange 25, and end cap 55 can be disposable, and can releasably engage the endoscope at one or more locations. For instance, end cap 55 can releasably engage the endoscope 100 at a distal end of the endoscope 100, and handle 60 can releasably engage the endoscope 100 at a proximal portion of the endoscope 100, as shown in FIG. 13. In FIG. 13, handle 60 can have an inwardly facing conical surface that engages an outwardly facing conical surface on endoscope 100.

FIG. 5A-5D show illustrative, non-limiting embodiments of cross sectional shapes of rail 30 and mating member 40 that allow sliding engagement of rail 30 and mating member 40. It will be understood that rail 30 and mating member 40 may take on various shapes and configurations, such that mating member 40 interlocks with the shape of rail 30 to allow sliding of mating member 40 along rail 30. As viewed in cross section, rail 30 can have opposing arms 31 which maintain engagement of mating member 40 with rail 30. Arms 31, together with the body of rail 30, can define a rail cavity 33 in which the mating member 40 can slide. If desired, arms 31 can be provided with a desired level of resilience, such as by material choice or dimensioning, so that mating member 40 can be caused to disengage from rail 30 (e.g. by "unzipping" from rail 30), such as if mating member 40 is urged radially outwardly from rail cavity 33. In an alternate embodiment, not shown, a wire may be employed as a rail 30 to provide a path along endoscope 100. Such a wire path may be attached at a distal and proximal end of endoscope 100, and provide a low-profile guide for accessory 50 to follow along endoscope 100.

The embodiment shown in FIG. 5D incorporates accessory 50 (in the form of a circular working channel) within mating member 40. This embodiment could enable the passage of accessories within a lumen of mating member 40 that slides inside rail 30. For example, rail 30 may have a substantially triangular recessed cross section that interlocks with mating member 40 having an outer contour of a triangular shape; and a medical device can slide within a lumen 42 located within mating member 40. This particular embodiment may be suitable for atraumatic passage of mating member 40 along rail 30, and when passing standard size accessories with guide system 20.

In yet another embodiment, mating member 40 can be sized and shaped to fit within rail cavity 33, and not extend above rail 30. In yet another embodiment, as an alternative to (or variation in) the combination of mating member 40 and accessory 50, a guide wire or guide tube having a generally circular cross-section could be disposed in rail cavity 33 for sliding engagement with rail 30. The guide wire or guide tube could have a diameter sized, relative to the size of rail cavity 33 and rail arms 31, such that the guide wire or guide tube can slide in rail cavity 33, while being maintained from disengaging from rail cavity 33 by rail arms 31.

Figure 6:
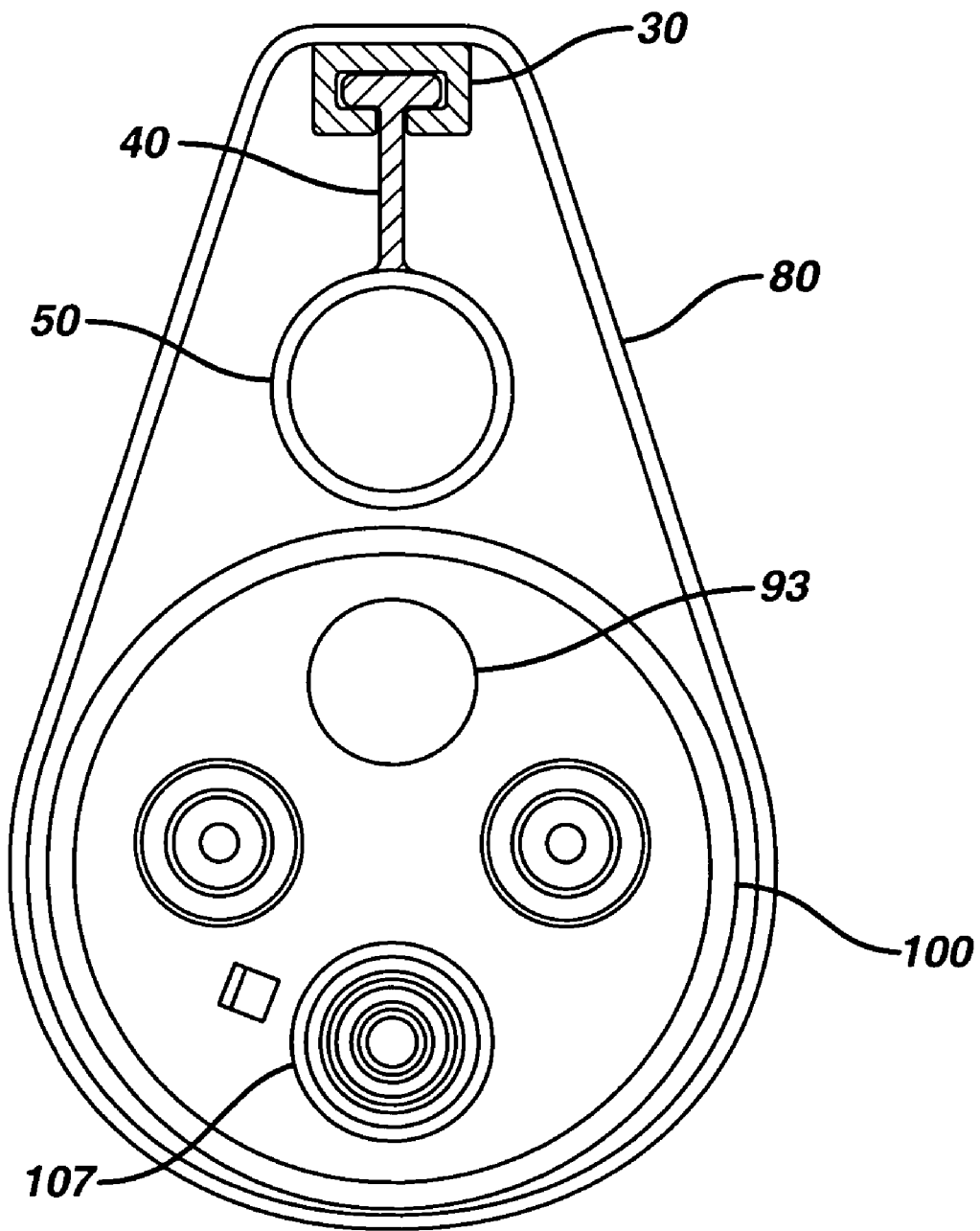
FIG. 6 is a cross section view of an embodiment of the guide system 20 according to the present invention showing an attachment means to connect guide system 20 to endoscope 100 through a sheath 80 with an inverted rail 30 disposed within the sheath 80.

FIG. 6 illustrates an alternate embodiment of attachment flange 25 to those shown in FIG. 1 and FIG. 2 for connecting rail 30 to endoscope 100. A sheath 80 surrounds endoscope 100 and rail 30. Rail 30 can be joined to an inner surface of sheath 80. Such an embodiment allows passage of mating member 40 and accessory 50 within sheath 80, providing for atraumatic passage along the tissue surface.

Figure 7:
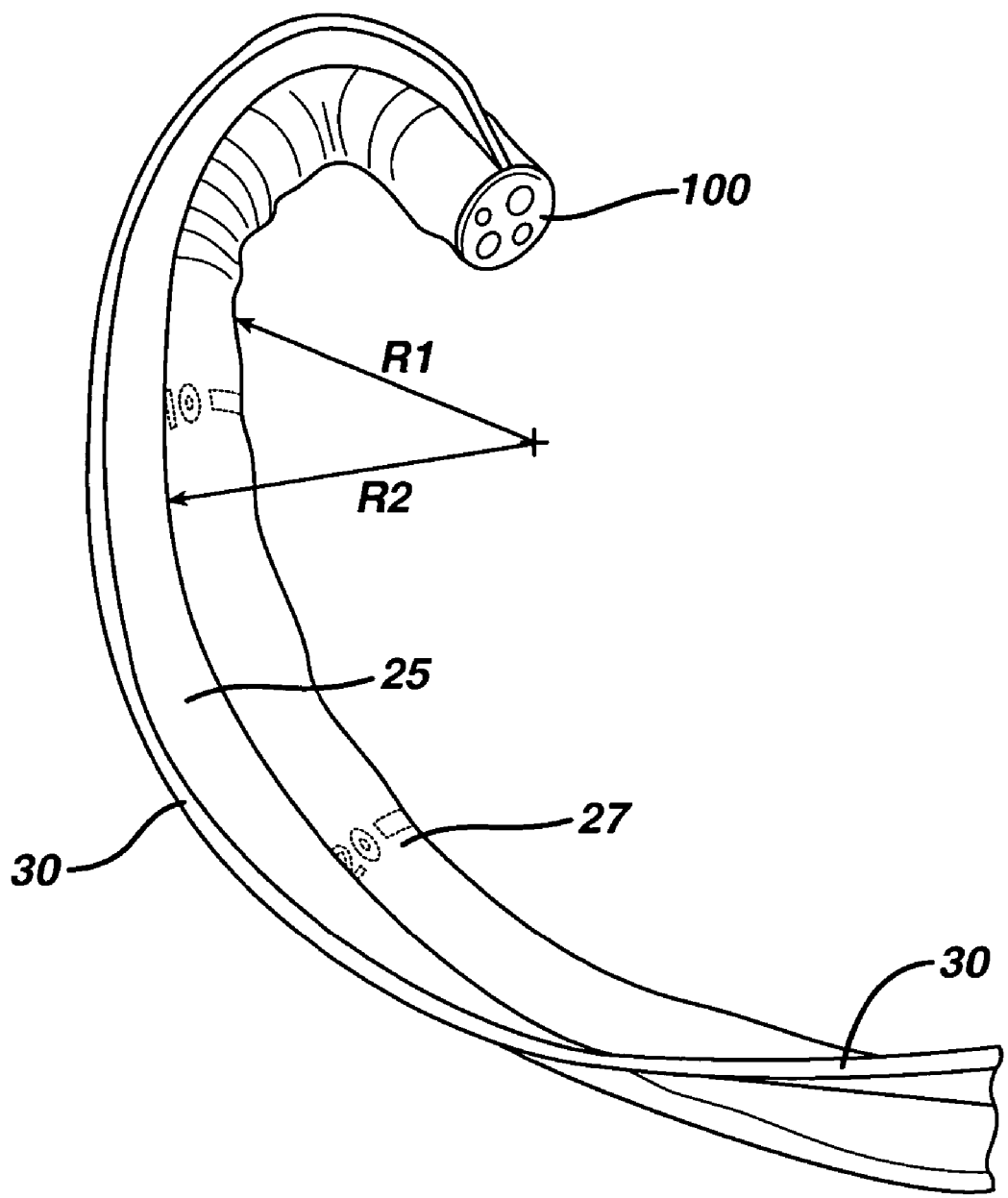
FIG. 7 is a side view endoscope 100 in a retroflexed curvature, showing rail 30 with a curvature radius R2 different from radius R1 of endoscope 100, and also showing the rail 30 and flange 25 folding or "warping" out of the plane of curvature of the endoscope, and such that rail 30 moves circumferentially relative to endoscope 100.

FIG. 7 shows a side view of rail 30 attached to endoscope 100 with one embodiment of attachment flange 25, showing how endoscope 100 and rail 30 are able to take on different curvatures, including different curved paths in different planes. The guide system 20 of the present invention provides support of the rail with respect to the endoscope 100 in a manner that decouples bending of rail 30 and flange 25 from bending of endoscope 100. Accordingly, guide system 20 does not prevent flexing of the endoscope 100. Commercially available flexible endoscopes 100 have the ability to retroflex (bend back to look upon itself) at its distal end. FIG. 7 illustrates this retroflex ability, and how rail 30 with attachment flange 25 is able to take on a path and radius of curvature that is different from the path and radius of curvature of the endoscope. Rail 30 can take on a radius of curvature that is some places (along the length of the endoscope 100) greater than, and in some places less than, the corresponding radius of curvature of the endoscope 100. Without being limited by theory, it is believed that the flexibility of the flange 25 and rail 30 permit the flange 25 and rail 30 to deform out of the plane of curvature of the endoscope to take on a path that reduces the elastic strain that would otherwise be present in the flange 25 and rail 30. In particular, the flexible flange 25 can permit the rail 30 to move into general or approximate alignment with the neutral axis of bending of the endoscope. Accordingly, the rail 30 is not fixed in an o'clock position relative to the endoscope that requires the rail 30 to be subject to tension or compression upon bending of the endoscope (as could be the case if the rail 30 where fixed at a certain circumferential position with respect to the cross section of the endoscope). This arrangement permits the operator to retroflex the endoscope 100, and therefore allows a user to use a normal technique to maneuver the endoscope 100 through the lumen.

By way of example, and without being limited by theory, one may consider bending of endoscope 100 with respect to bending a beam. In beam bending, there is a neutral axis (generally in the center of the beam for symmetric beam cross sections), with one beam surface being in compression, the opposite surface being in tension. A rail supported on an endoscope in such a manner that the rail is subject to tensile stress or compressive stresses upon bending of the endoscope may impede bending of endoscope 100 because of the rail's resistance to tension and/or compression.

The illustration in FIG. 7 shows how a flexible attachment flange 25 can minimize the affect of rail 30 on endoscope 100 bending. The height of attachment flange 25 effectively tethers rail 30 to endoscope 100, but allows rail 30 to find a path of different curvature and/or move circumferentially with respect to the endoscope. In compression, attachment flange 25 permits rail 30 pleat or otherwise deform (such as in a wavy fashion), minimizing the effect on endoscope 100 bending. In embodiments including a flexible thin wall tube/sheath 27, the decoupling of bending of the rail from bending of the endoscope can be further enhanced due to the ability to accommodate circumferential movement of the tube or sheath 27 with respect to the endoscope.

Figure 8:
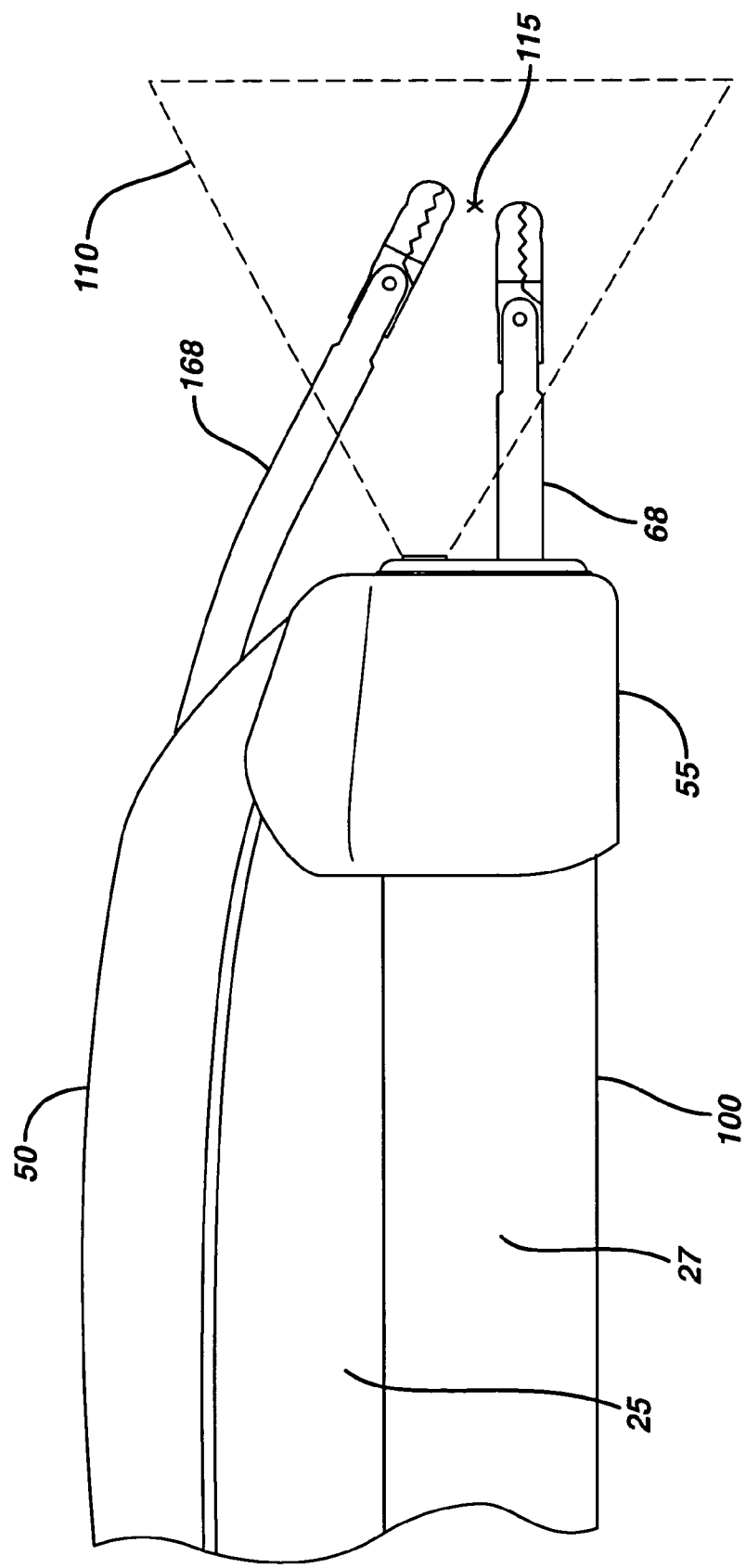
FIG. 8 is a side view of rail 30 associated with an end cap 55 to direct a non-articulating medical instrument 168 extending from an accessory 50 (in the form of a guide tube 50) into field of view 110 at a convergence point 115 with an instrument 68 extending from an integral channel 93 of endoscope 100.

FIG. 8 illustrates how end cap 55 may be used to hold a distal end of rail 30 to endoscope 100 and present accessory 50 or instrument 168 into field of view 110. Guide system 20 provides a convergence point 115 for a medical instrument 168 extending from an accessory 50 (in the form of an external guide channel in FIG. 8) and an instrument 68 extending from an integral working channel 93 of endoscope 100. This feature allows accessory 50 and instrument 168 to be used in conjunction with instrument 68 to perform multiple-handed therapy or diagnosis, such that instrument 168 and instrument 68 are not required to have separate articulation capabilities. In contrast, an endoscope configuration that does not provide the guided convergence (such as at point 115) of the present invention would typically require one or more instruments to have an articulation feature or other mechanism for providing curvature at the instrument's distal end if it is desired to have one instrument cooperate with another in the endoscope's field of view.

Figure 9:
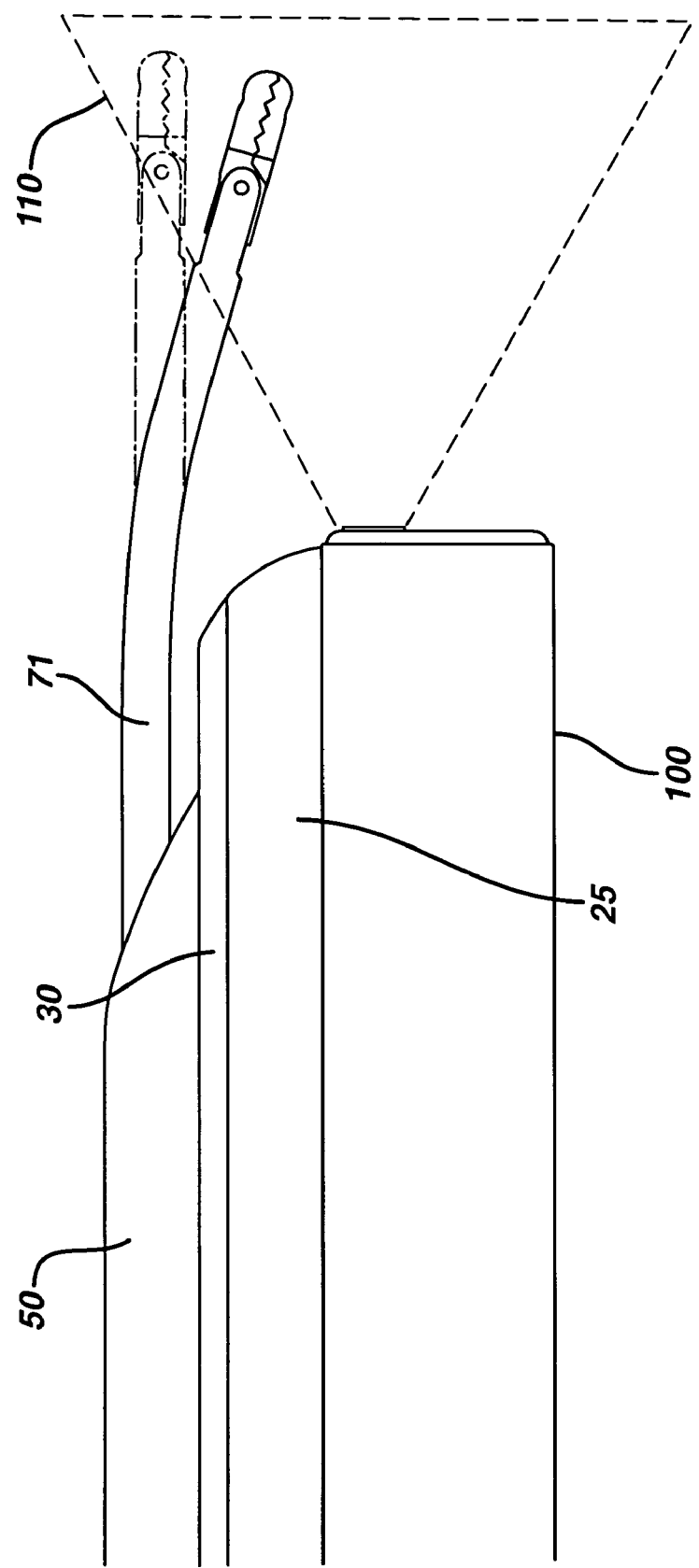
FIG. 9 shows a side view of an embodiment of guide system 20 without end cap 55 being used with an articulating accessory 71 used to position the distal end of accessory 71 into the field of view 110.

Referring to FIG. 9, if the guided convergence of end cap 55 is not provided, cooperation of multiple instruments (such as at convergence point 115) in field of view 110 would require one of instruments (such as instrument 77 in FIG. 9) to have a built in articulation capability. End cap 55 with angle 65 allows a user to use standard, non-articulating, accessories or instruments to achieve new therapies or diagnoses.

Figure 10:
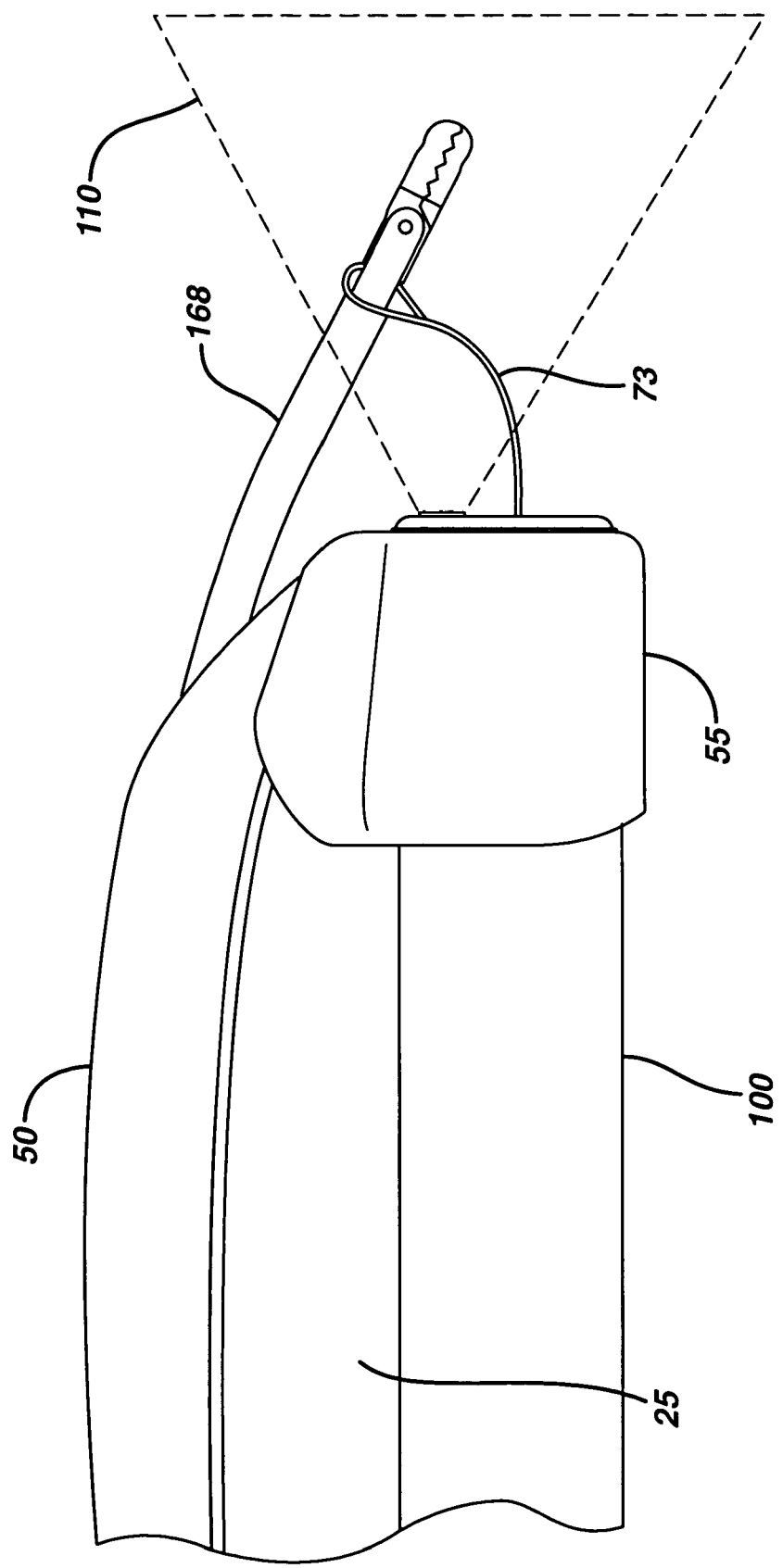
FIG. 10 is an isometric view showing one technique that may be used to direct instrument 168 from accessory 50 into field of view 110 with a snare 73 extending from integral channel 93.

FIG. 10 shows a guidance system 20 of the present invention and illustrates a method of articulating an instrument (such as instrument 168 extending from accessory 50) with a snare 73 extending from integral channel 93 of endoscope 100. The snare 73 can be in the form of a looped wire, and can be advanced from channel 93 to meet an instrument 168 extending from accessory 50. Once the instrument 168 extends through the loop in snare 73, the curvature of instrument 168 can be increased by advancing instrument 168 from accessory 50, and/or by retracting snare 73 in channel 93. Accordingly, the instrument 168 can be positioned at a desired site (such as a tissue site on the wall of the GI tract).

FIGS. 11A-C illustrate an additional advantage of use of the end cap 55 of the present invention. FIGS. 11A-C illustrate the end cap 55 positioned at various o'clock positions on the distal end of endoscope 100. End cap 55 can be positioned on the endoscope 100 so that accessory 50 is located in a desired o'clock position with respect to one or more features of the endoscope, such as integral working channel 93 or optics/viewing lens 107. For instance, in some applications it may be desirable to have the integral channel 93 positioned at a certain distance with respect to accessory 50 to perform a procedure, while in other applications it may be desireable to position the viewing lens 107 at a particular position relative to accessory 50 to obtain a desired field of view.

Figure 12A:
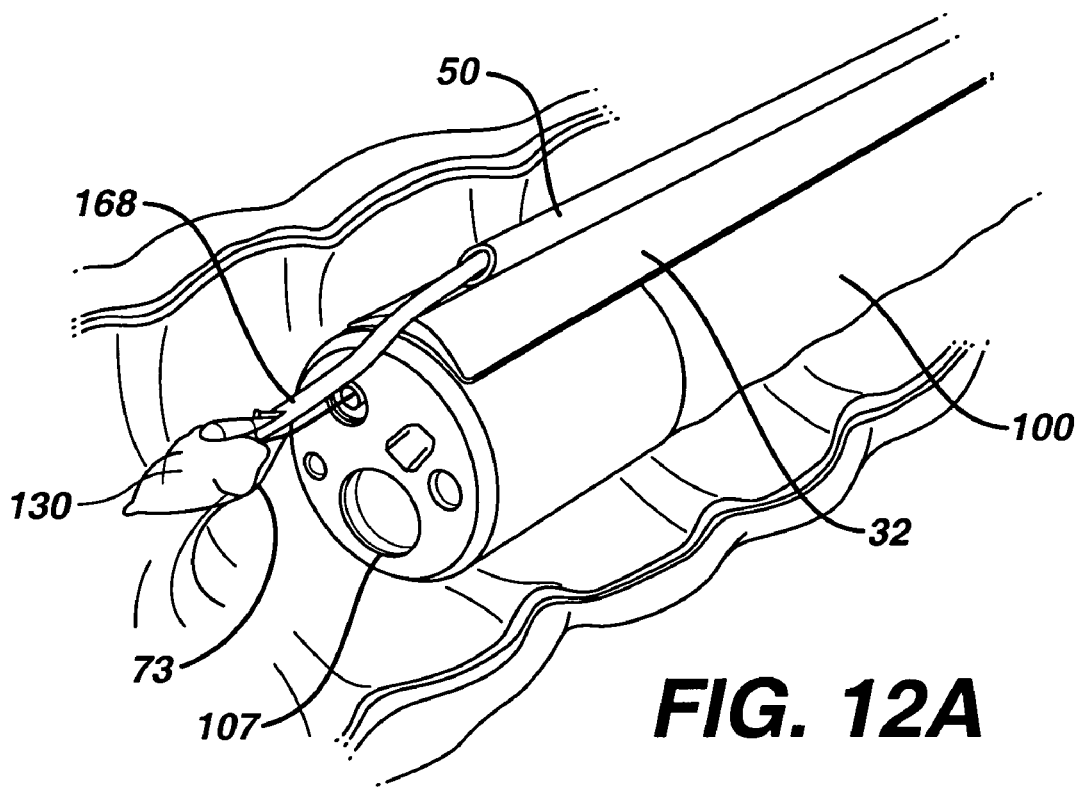
FIGS. 12A and 12B are isometric views of one method of using guide system 20 with accessory 50 and instrument 68 to remove a tissue 130 without removing endoscope 100 from its position within the patient.
Figure 12B:
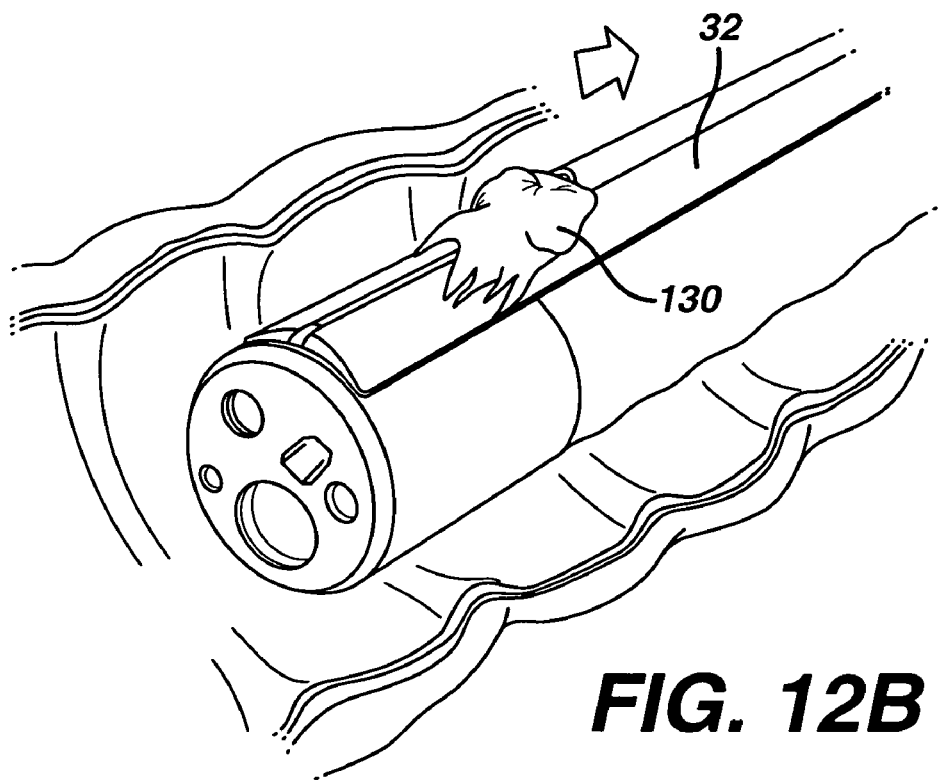

FIGS. 12A and 12B illustrate an alternative embodiment in which guide system 20 comprises an adhesive-backed elastically extensible rail, the elastically extensible rail designated by numeral 32 in FIGS. 12A and 12B. Elastically extensible rail 32 can be formed of a suitable elastically extensible material, so that rail 32 elongates in tension and folds, buckles, or otherwise bends in compression when endoscope is bent or otherwise flexed during use. Rail 32 accommodates bending of the endoscope without substantially altering the bending stiffness of the endoscope. A suitable material for rail 32 is Santoprene Thermoplastic Rubber (Advanced Elastomer Systems, Akron, Ohio), and a suitable flexible adhesive for attaching rail 30 directly to the outside surface of the endoscope is Super 77 Spray adhesive (3M, St. Paul, Minn.). Such an embodiment allows rail 32 to change in length or otherwise deform as endoscope 100 is bent, and may be used in embodiments where a flexible flange 25 is not provided.

In FIGS. 12A and 12B, a tissue mass is shown being captured and severed by a snare 73 extending from a working channel of the endoscope, and grasped by an instrument 168, such as a flexible forceps. The flexible forceps extends through accessory 50 (which is in the form of a flexible guide tube in FIG. 12A), and the flexible forceps can then be used to withdraw the severed tissue mass from the gastrointestinal tract through the accessory 50.

FIGS. 12A and 12B show one of numerous treatment methods that may be enabled by guide system 20. Removal of multiple biopsies of a tissue 130, such as large polyps currently requires removal of endoscope 100 with the tissue sample 130. This can be time consuming, especially if the physician needs to re-introduce the endoscope 100 through a tortuous colon. FIGS. 12A and 12B illustrates how guide system 20 would provide a way to remove such an incised polyp without removing the endoscope 100.

FIG. 13 is a cross section view of a proximal end of guide system 20, including a cross section of the attachment of handle 60 to endoscope 100. One component of handle 60 is a guide bar 76 that can be provided (such as by attachment to handle 60) to prevent unintentional disengagement of mating member 40 from rail 30. Mating member 40 can be fed between the guide bar 76 and the body of handle 60 into funnel feature 37. Guide bar 76 can prevent mating member 40 from being inadvertently "peeled" out of or "unzipped" from rail 30 at its proximal end.

In use, a distal end of endoscope 100 can be inserted through the bore in handle 60, through sheath 27, and into the bore of end cap 55. Releasable connections of handle 60 and end cap 55 to endoscope 100 may then be made to hold guide system 20 in place during a procedure. The inner diameter of sheath 27 is preferably sized to allow insertion of endoscope 100 without the need for a lubricant between endoscope 100 and sheath 27. To achieve this, a nominal clearance of at least about 0.040" may be provided between the diameter of endoscope 100 and the inner diameter of sheath 27.

The endoscope 100 with rail 30 can then inserted into the body of a patient. When desired, the physician can then introduce mating member 40 into a funnel feature 37 and slide accessory 50 with mating member 40 along rail 30 into the body of a patient. Accessory 50 may be a working channel, through which instrument 168 may be introduced. The physician can then extend instrument 168 into a field of view 110 to perform a procedure.

While accessory 50 has been described primarily as an additional working channel, it will be understood that accessory 50 can take other forms. Other devices which can be provided as suitable accessories include, but are not limited to, a biopsy forceps, an articulating instrument, a surgical scissor, a device adapted for sewing or stapling tissue, a guidewire, a device adapted for liquid or gas injection, or a tissue ablation system. For instance, various medical instruments could be could be modified to include a mating member configured to fit and slide in rail 30 (e.g. such as by permanently or non-permanently attaching a mating member 40 to the instrument). Or, alternatively, the rail cavity 33 and rail arms 31 can be sized and shaped to accept a particular medical instrument for sliding engagement in rail cavity 33.

Additionally, a plurality of endoscopes 100 can be connected to each other using guide system 20 by attaching rail 30 to one "parent" endoscope 100, and attaching mating member 40 to a second "daughter" endoscope. Such an arrangement would allow the scopes to be connected and slide relative to each other, providing multiple perspectives of an object within the body of a patient.

Those skilled in the art will also recognize that a plurality of rails 30 may be attached to endoscope 100 to provide multiple paths for instruments to be fed along the outside of endoscope 100. The plurality of rails 30 may be attached to a plurality of attachment flanges 25 or to a common attachment flange 25.

FIG. 14 illustrates an embodiment of a guide system 20 wherein rail 30 is wound in a generally helical fashion about an endoscope 100. For instance, the distal end of rail 30 can be joined to the distal end of an endoscope 100, the rail 30 can be wound in a helical manner and in a proximal direction along the endoscopes length, with a proximal end of the rail 30 being joined to a proximal portion of the endoscope. In FIG. 14, the distal end of rail 30 is shown associated with an end cap 55. In one embodiment, a guide system 20 can comprise a handle 60, an end cap 55, and a rail 30 extending intermediate the handle 60 and the end cap 55, in which embodiment the flange 25 and flexible tube 27 may be omitted if desired. The end cap 55 can be attached to the distal end of the endoscope, and the rail 30 can be wound loosely about endoscope 100 (or extended in a generally linear fashion along the endoscope 100 with sufficient slack in rail 30 to allow rail 30 to accommodate bending of the endoscope).

Figure 15:
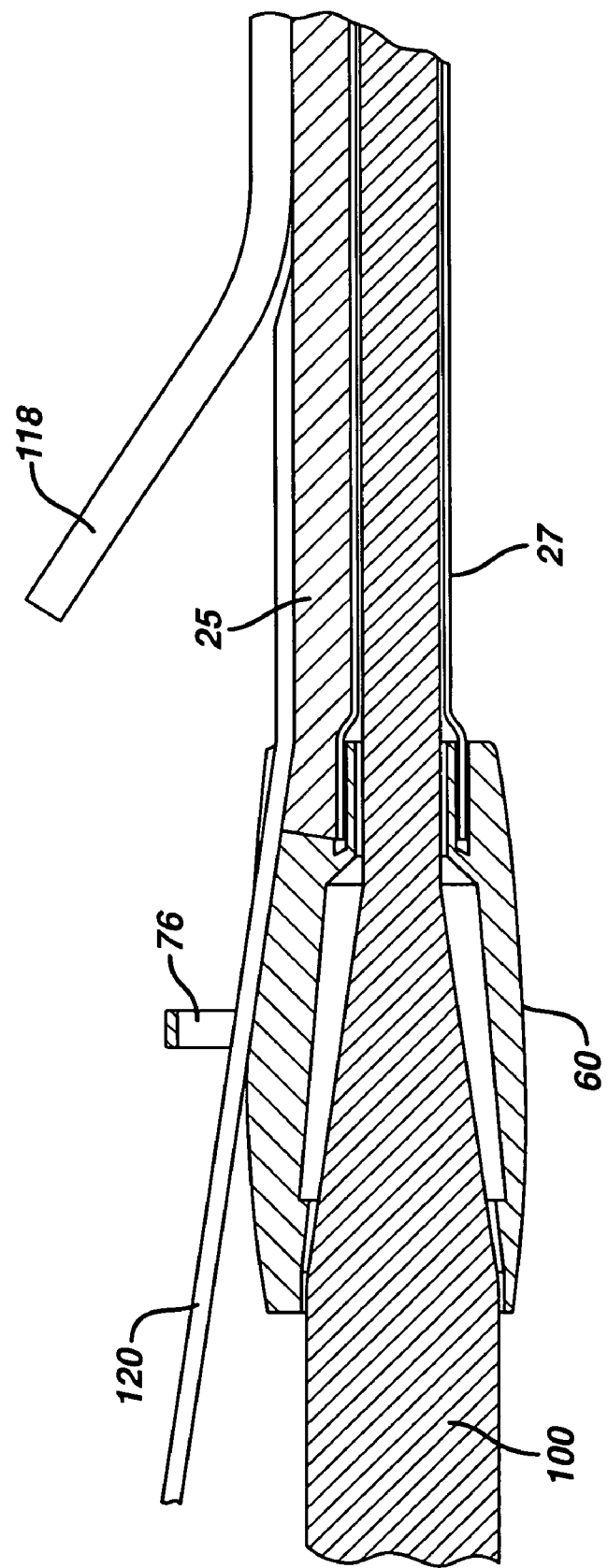
FIG. 15 is a cross section view showing a proximal end of endoscope 100 with an arrangement of a second mating member 120 being used to disengage a first device 118 from rail 30.

FIG. 15 is a cross section view showing a proximal end of a guide system 20 attached to endoscope 100. One method of using guide system 20 may be to introduce a first device 118 into the body of a patient by intentionally disengaging first device 118 from rail 30 with a second mating member 120. This can be achieved by first introducing first device 118 into rail 30, then disengaging a proximal end of first device 118 from rail 30 (e.g by pulling the proximal end of first device 118 upward in the plane of FIG. 15 to disengage the proximal end of first device 118 from the rail 30), and then introducing the second mating member 120 into sliding engagement with the rail, so that second mating member 120 is disposed between the first device 118 and rail 30 to effectively "unzip" first device 118 from rail 30 as second mating member 120 is advanced distally down the length of rail 30.

For example, first device 118 may be a guidewire, a feeding tube (e.g. to be placed in the esophageal lumen to extend from the oral cavity to the stomach), a duct for conveying a liquid or gas, or any other instrument that is meant to be positioned within a body lumen for temporary or permanent placement. The rail 30 can be positioned within the body lumen, such as by being associated with an endoscope which is introduced into the body lumen. The first device can be introduced onto rail 30 and advanced distally along the rail into a predetermined position within the body. A proximal end of the device 118 can then be disengaged from the rail, as shown in FIG. 15. The second mating member 120 can then be introduced under guide bar 76 and into engagement with the rail 30, and advanced axially along the rail in a distal direction to force the device 118 out of engagement with the rail 30, thereby leaving device 118 in place in the body lumen. Advancing second mating member 120 along the rail 30, wherein member 120 is interposed between rail 30 and device 118, causes the device 118 to be urged out of the rail 30 and deployed in a direction generally perpendicular to the rail 30. As shown in FIG. 15, member 120 can have a tapered distal end to enhance the ability of member 120 to be interposed between rail 30 and device 118 for urging device 118 out of engagement with rail 30.

Referring again to FIG. 16, the guide system 20 of the present invention can provide advancement and positioning of a relatively rigid and straight device 125 along a curved portion of an endoscope 100. In FIG. 16, the device 125 can be pushed by or carried on a mating member 40. The portion of the track 30 on which device 125 is positioned can be relatively straight, in comparison with the corresponding portion of the endoscope which is curved.

While various embodiments of the present invention have been disclosed, it will be obvious to those skilled in the art that such embodiments are provided by way of example only. The present invention may be provided in kit form with other medical devices, including medical devices useful in the working channel of an endoscope, or with an endoscope. The kit elements can be pre-sterilized and packaged in a sealed container or envelope to prevent contamination. The present invention may be provided as a single use disposable device, or alternatively, may be constructed for multiple uses. Further, each element or component of the present invention may be alternatively described as a means for performing the function or functions performed by the element or component. Numerous variations, changes, and substitutions will now occur to those skilled in the art without departing from the invention. Accordingly, it is intended that the invention be limited only by the spirit and scope of the appended claims.

What is claimed is:

1. A medical apparatus comprising:
 a flexible sheath sized to receive an endoscope;
 an end cap having a length less than that of the flexible sheath and disposed at a distal end of the flexible sheath, the end cap adapted to releasably engage the distal end of an endoscope received within the flexible sheath, the end cap having an open distal end and a longitudinal axis, and wherein the end cap comprises a through bore for receiving the distal end of the endoscope to hold the end cap in fixed relationship with respect to the distal end of the endoscope, wherein the end cap has an outer surface, the outer surface having a slot formed therein, the slot disposed radially outwardly of the through bore and the slot inclined radially inwardly from a proximal end of the slot to a distal end of the slot; and a flexible track having a length longer than that of the end cap, wherein the flexible track is configured to engagingly receive and guide an accessory, external to the track, along at least a portion of the length of the flexible sheath, wherein at least a portion of a length of the flexible track is supported along the outer surface of the flexible sheath; and wherein a distal portion of the track extends into the slot in the end cap and is held in a the end cap comprises an outer surface feature for holding the distal portion of the flexible track in a fixed radially inwardly inclined configuration with respect to the longitudinal axis of the end cap.

2. The medical apparatus of claim 1 wherein the track has a length of at least 50 cm.

3. The medical apparatus of claim 1 wherein the track has a length of at least 100 cm.

4. The medical apparatus of claim 1 wherein the track is non-tubular.

5. The medical apparatus of claim 1 wherein the track comprises a rail.

* * * * *